(12) United States Patent
Zhamu et al.

(10) Patent No.: US 11,414,409 B2
(45) Date of Patent: Aug. 16, 2022

(54) HUMIC ACID-BONDED METAL FOIL FILM CURRENT COLLECTOR AND BATTERY AND SUPERCAPACITOR CONTAINING SAME

(71) Applicant: Global Graphene Group, Inc., Dayton, OH (US)

(72) Inventors: Aruna Zhamu, Springboro, OH (US); Bor Z. Jang, Centerville, OH (US)

(73) Assignee: Global Graphene Group, Inc., Dayton, OH (US)

( * ) Notice: Subject to any disclaimer, the term of this patent is extended or adjusted under 35 U.S.C. 154(b) by 162 days.

(21) Appl. No.: 16/788,649

(22) Filed: Feb. 12, 2020

(65) Prior Publication Data

US 2020/0255419 A1 Aug. 13, 2020

Related U.S. Application Data

(62) Division of application No. 15/243,606, filed on Aug. 22, 2016, now Pat. No. 10,597,389.

(51) Int. Cl.
*C07D 413/14* (2006.01)
*H01M 4/66* (2006.01)
(Continued)

(52) U.S. Cl.
CPC ............ *C07D 413/14* (2013.01); *C01B 32/20* (2017.08); *C09K 5/14* (2013.01); *H01G 11/02* (2013.01);
(Continued)

(58) Field of Classification Search
CPC ......... Y02E 60/13; Y02E 60/10; H01G 11/28; H01G 11/02; H01G 11/36; H01G 11/68;
(Continued)

(56) References Cited

U.S. PATENT DOCUMENTS 3,671,427 A 6/1972 Andrews, Jr. et al.
4,568,412 A 2/1986 Atkins, Jr. et al.
(Continued)

FOREIGN PATENT DOCUMENTS

CN 1230972 A 10/1999
CN 101798465 A 8/2010
(Continued)

OTHER PUBLICATIONS

Franklin 1951.
(Continued)

*Primary Examiner* — Jonathan G Jelsma
*Assistant Examiner* — Omar M Kekia

(57) ABSTRACT

A humic acid-bonded metal foil current collector in a battery or supercapacitor, comprising: (a) a thin metal foil having two opposed but parallel primary surfaces; and (b) a thin film of humic acid (HA) or a mixture of HA and graphene, having hexagonal carbon planes, wherein HA or both HA and graphene are chemically bonded to at least one of the two primary surfaces; wherein the thin film has a thickness from 10 nm to 10 μm, an oxygen content from 0.01% to 10% by weight, an inter-planar spacing of 0.335 to 0.50 nm between hexagonal carbon planes, a physical density from 1.3 to 2.2 g/cm³, all hexagonal carbon planes being oriented substantially parallel to each other and parallel to the primary surfaces, exhibiting a thermal conductivity greater than 500 W/mK, and/or electrical conductivity greater than 1,500 S/cm when measured alone without the metal foil.

4 Claims, 17 Drawing Sheets

(51) Int. Cl.

| | | |
|---|---|---|
| *H01G 11/68* | (2013.01) | |
| *H01G 11/84* | (2013.01) | |
| *C09K 5/14* | (2006.01) | |
| *C01B 32/20* | (2017.01) | |
| *H01G 11/04* | (2013.01) | |
| *H01G 11/02* | (2013.01) | |
| *H01G 11/36* | (2013.01) | |
| *H01G 11/28* | (2013.01) | |
| *H01G 11/70* | (2013.01) | |
| H01M 10/052 | (2010.01) | |
| H01M 12/08 | (2006.01) | |
| H01M 4/1393 | (2010.01) | |
| H01M 4/04 | (2006.01) | |
| H01M 10/0525 | (2010.01) | |
| H01M 4/133 | (2010.01) | |
| H01M 4/583 | (2010.01) | |

(52) U.S. Cl.
CPC ............. *H01G 11/04* (2013.01); *H01G 11/28* (2013.01); *H01G 11/36* (2013.01); *H01G 11/68* (2013.01); *H01G 11/70* (2013.01); *H01G 11/84* (2013.01); *H01M 4/661* (2013.01); *H01M 4/663* (2013.01); *H01M 4/667* (2013.01); *H01M 4/04* (2013.01); *H01M 4/133* (2013.01); *H01M 4/1393* (2013.01); *H01M 4/583* (2013.01); *H01M 4/66* (2013.01); *H01M 10/052* (2013.01); *H01M 10/0525* (2013.01); *H01M 12/08* (2013.01); *Y02E 60/10* (2013.01)

(58) Field of Classification Search
CPC ........ H01G 11/04; H01G 11/70; H01G 11/84; H01M 4/583; H01M 4/663; H01M 10/052; H01M 4/04; H01M 4/1393; H01M 4/667; H01M 4/133; H01M 12/08; H01M 10/0525; H01M 4/661; H01M 4/66; C07D 413/14; C09K 5/14; C01B 32/20
USPC ....................................................... 429/231.8
See application file for complete search history.

(56) References Cited

U.S. PATENT DOCUMENTS

| | | | |
|---|---|---|---|
| 5,688,999 | A | 11/1997 | Lebo et al. |
| 6,872,330 | B2 | 3/2005 | Mack et al. |
| 6,913,154 | B2 | 7/2005 | Koslow |
| 7,022,176 | B1 | 4/2006 | Inoue et al. |
| 7,071,258 | B1 | 7/2006 | Jang et al. |
| 7,327,000 | B2 | 2/2008 | DeHeer et al. |
| 7,623,340 | B1 | 11/2009 | Song et al. |
| 7,758,842 | B2 | 7/2010 | Nishikawa et al. |
| 7,948,739 | B2 | 5/2011 | Zhamu et al. |
| 8,105,565 | B2 | 1/2012 | Nishikawa et al. |
| 9,053,870 | B2 | 6/2015 | Yu et al. |
| 9,233,850 | B2 | 1/2016 | Jang et al. |
| 9,437,372 | B1 | 9/2016 | Zhamu et al. |
| 2002/0085968 | A1 | 7/2002 | Smalley et al. |
| 2003/0034295 | A1 | 2/2003 | Strano et al. |
| 2003/0108785 | A1 | 6/2003 | Wu et al. |
| 2004/0013942 | A1 | 1/2004 | Fukumoto et al. |
| 2005/0271547 | A1 | 12/2005 | Gerber et al. |
| 2005/0271574 | A1 | 12/2005 | Jang et al. |
| 2007/0209506 | A1 | 9/2007 | Liu et al. |
| 2008/0048152 | A1 | 2/2008 | Jang et al. |
| 2008/0248275 | A1 | 10/2008 | Jang et al. |
| 2009/0061312 | A1 | 3/2009 | Zhamu et al. |
| 2009/0095942 | A1 | 4/2009 | Yamaguchi et al. |
| 2010/0021819 | A1 | 1/2010 | Zhamu et al. |
| 2010/0035093 | A1 | 2/2010 | Ruoff et al. |
| 2010/0085713 | A1 | 4/2010 | Balandin et al. |
| 2010/0140792 | A1 | 6/2010 | Haddon et al. |
| 2011/0108978 | A1 | 5/2011 | Kim et al. |
| 2011/0159372 | A1 | 6/2011 | Zhamu et al. |
| 2011/0165321 | A1 | 7/2011 | Zhamu et al. |
| 2011/0165466 | A1 | 7/2011 | Zhamu et al. |
| 2011/0201739 | A1 | 8/2011 | Beall |
| 2011/0243830 | A1 | 10/2011 | Ozaki et al. |
| 2011/0262377 | A1 | 10/2011 | McKay et al. |
| 2012/0021250 | A1 | 1/2012 | Lee et al. |
| 2012/0088154 | A1 | 4/2012 | Liu et al. |
| 2013/0005013 | A1 | 1/2013 | Sabbah et al. |
| 2013/0095389 | A1 | 4/2013 | Bhardwaj et al. |
| 2013/0112925 | A1 | 5/2013 | Beall |
| 2013/0140495 | A1 | 6/2013 | Beall |
| 2013/0141774 | A1 | 6/2013 | McCarthy |
| 2013/0171339 | A1 | 7/2013 | Wang et al. |
| 2013/0224603 | A1 | 8/2013 | Chen et al. |
| 2014/0030590 | A1 | 1/2014 | Wang et al. |
| 2014/0030636 | A1 | 1/2014 | Zhao et al. |
| 2014/0110049 | A1 | 4/2014 | Yuen et al. |
| 2014/0234702 | A1 | 8/2014 | Zhang et al. |
| 2014/0315083 | A1 | 10/2014 | Liu et al. |
| 2014/0335420 | A1 | 11/2014 | Yamamoto et al. |
| 2015/0044364 | A1 | 2/2015 | Katayama et al. |
| 2015/0084603 | A1 | 3/2015 | Thillaiyan et al. |
| 2015/0086881 | A1* | 3/2015 | Zhamu .................. H01G 11/36 429/405 |
| 2015/0118554 | A1* | 4/2015 | Wu ...................... H01M 10/052 429/217 |
| 2015/0218003 | A1 | 8/2015 | Zhamu et al. |
| 2015/0259212 | A1 | 9/2015 | Li et al. |
| 2015/0266739 | A1 | 9/2015 | Zhamu et al. |
| 2016/0043384 | A1 | 2/2016 | Zhamu et al. |
| 2016/0079001 | A1 | 3/2016 | Lin et al. |
| 2016/0118668 | A1 | 4/2016 | DuPasquier et al. |
| 2016/0240840 | A1 | 8/2016 | He et al. |

FOREIGN PATENT DOCUMENTS

| | | |
|---|---|---|
| CN | 103641117 A | 3/2014 |
| CN | 104600320 A | 5/2015 |
| CN | 103752281 B | 4/2016 |
| CN | 104900876 B | 5/2017 |
| GB | 317496 A | 8/1929 |
| GB | 2103633 B | 7/1983 |
| JP | 58117649 | 7/1983 |
| JP | S58173138 A | 10/1983 |
| JP | S59100168 A | 6/1984 |
| WO | 2012151880 A1 | 11/2012 |

OTHER PUBLICATIONS

Gomes de Melo 2015.
SPEIGHT 2017 Rules of Thumb for Petroleum Engineers.
U.S. Appl. No. 15/228,133 Final Office Action dated Jan. 8, 2021, 10 pages.
U.S. Appl. No. 15/251,857 Final Office Action dated Aug. 27, 2020, 42 pages.
U.S. Appl. No. 15/251,857 Nonfinal Office Action dated Feb. 4, 2021, 51 pages.
U.S. Appl. No. 16/017,339 Final Office Action dated Sep. 11, 2020, 13 pages.
U.S. Appl. No. 16/017,339 Nonfinal Office Action dated Mar. 12, 2021, 12 pages.
U.S. Appl. No. 16/409,177 Nonfinal Office Action dated Apr. 13, 2021, 11 pages.
U.S. Appl. No. 16/814,734 Final Office Action dated Sep. 25, 2020, 17 pages.
U.S. Appl. No. 16/814,734 Nonfinal Office Action dated Jun. 12, 2020, 16 pages.
Anderson et al., "The Use of Esters of N-Hydroxysuccinimide in Peptide Synthesis" J. Amer. Chem. Soc. (1964) vol. 86, No. 9, pp. 1839-1842.
Chen et al., "Three-dimensional Flexible and Conductive Interconnected Graphene Networks Grown by Chemical Vapor Deposition" Nature Materials (2011) vol. 10, pp. 424-428.

(56) References Cited

OTHER PUBLICATIONS

Choi et al., "3D Macroporous Graphene Frameworks for Supercapacitors with High Energy and Power Densities" ACS Nano (2012) vol. 6, pp. 4020-4028.
CN 103641117a, Google Patent English language translation, 5 pages.
CN 103752281B, Google Patent English language translation, 8 pages.
CN 104600320A Google Patent English Translation, 6 pages.
CN 1230972A, Google Patents English language translation, 22 pages.
CN104600320A—English language translation from Google Patent—https://patents.google.com/patent/CN104600320A/en, 6 pages.
Duraia et al., "Reduced humic acid nanosheets and its uses as nanofiller" J. Phys. Chem. Solids (2015) vol. 85, pp. 36-90.
PCT/US17/43494 International Search Report and Written Opinion dated Sep. 27, 2017, 15 pages.
PCT/US17/43605 International Search Report and Written Opinion dated Sep. 27, 2017, 10 pages.
PCT/US17/43619 International Search Report and Written Opinion dated Oct. 18, 2017, 18 pages.
Polrolniczak et al., "Humic Acid-Derived Mesoporous Carbon as Cathode Component for Lithium-Sulfur Battery" Int. J. Electrochem. Sci. (2015) vol. 10, pp. 9370-9378.
Polrolniczak, "Humic Acid-Derived Mesoporous Carbon as Cathode Component for Lithium-Sulfur Batter" International Journal of Electrochemical Science (2015) vol. 10, pp. 9370-9378.
Porada et al., "Review on the science and technology of water desalination by capacitive deionization" Progress in Materials Science (2013) vol. 58, pp. 1388-1442.
Powell et al., "Graphene Oxide and graphene from low grade coal: Synthesis, characterization and applications" Current Opinion in Colloid & Interface Science (2015) vol. 20, No. 5, pp. 362, 365-366.
Prabakar et al., "Graphene oxide as a corrosion inhibitor for the aluminum current collector in lithium ion batteries" Carbon (2013) vol. 52, pp. 128-136.
Rice et al., "Statistical evaluation of the elemental composition of humic substances" Org. Geochem. (1991) vol. 17, No. 5, pp. 635-648.
Stevenson, Humus Chemistry: Genesis, Composition, Reactions (1982) pp. 258-263, John Wiley & Sons, New York.
U.S. Appl. No. 15/228,133 Nonfinal Office Action dated Aug. 8, 2019, 8 pages.
U.S. Appl. No. 15/240,537 Final Office Action dated Oct. 10, 2019, 7 pages.
U.S. Appl. No. 15/240,537 Non-final Office Action dated Apr. 4, 2019, 11 pages.
U.S. Appl. No. 15/243,589 Nonfinal Office Action dated Nov. 16, 2017, 8 pages.
U.S. Appl. No. 15/243,589 Response Nonfinal Office Action dated Nov. 22, 2017, 11 pages.
U.S. Appl. No. 15/243,606 Nonfinal Office Action dated May 2, 2019, 15 pages.
U.S. Appl. No. 15/251,841 Nonfinal Office Action dated Jan. 2, 2019, 5 pages.
U.S. Appl. No. 15/251,841 Nonfinal Office Action dated Jul. 1, 2019, 7 pages.
U.S. Appl. No. 15/251,849 Final Office Action dated Jul. 25, 2019, 14 pages.
U.S. Appl. No. 15/251,849 Nonfinal Office Action dated Nov. 1, 2017, 21 pages.
U.S. Appl. No. 15/251,857 Final Office Action dated Nov. 13, 2019, 42 pages.
U.S. Appl. No. 15/251,857 Nonfinal Office Action dated Apr. 3, 2020, 42 pages.
U.S. Appl. No. 15/251,857 Nonfinal Office Action dated May 29, 2019, 37 pages.
U.S. Appl. No. 15/270,868 Final Office Action dated Jul. 25, 2019, 11 pages.
U.S. Appl. No. 15/270,868 Non-final Office Action dated Mar. 28, 2019, 10 pages.
U.S. Appl. No. 15/270,868 Nonfinal Office Action dated Nov. 1, 2017, 23 pages.
U.S. Appl. No. 16/017,339 Nonfinal Office Action dated Mar. 6, 2020, 9 pages.
Wang et al., "Graphene-coated plastic film as current collector for lithium/sulfur batteries" J. Power Source (2013) vol. 239, pp. 623-627.
WO 2012151880A1—English language translation from Google Patent—https://patents.google.com/patent/WO2012151880A1/en, 15 pages.
Wunderwald et al., "Formation and degradation of a synthetic humic acid derived from 3-fluorocatechol" Applied Microbiology and Biotechnology (2000) vol. 53, No. 4, p. 441.
Xi et al., "Binder free three-dimensional sulphur/few-layer graphene foam cathode with enhanced high-rate capability for rechargeable lithium sulphur batteries" Nanoscale (2014) vol. 6, No. 11, pp. 5746-5753.
Xu et al., "Self-Assembled Graphene Hydrogel via a One-Step Hydrothermal Process" ACS Nano (2010) vol. 4, No. 7, pp. 4324-4330.
Yang et al., "Two-dimensional Graphene Nano-ribbons" J. Am. Chem. Soc. (2008) vol. 130, pp. 4216-4217.
El-Shazly et al., "Reduced humic acid nanosheets and its uses as nanofiller" Journal of Physics and Chemistry of Solids (2015) vol. 85, pp. 86-90.
Gwon et al., "Flexible energy storage devices based on graphene paper" Energy and Environmental Science (2011) vol. 4, pp. 1277-1283.
Hummers et al., "Preparation of graphitic oxide" J. Am. Chem. Soc. (1958) vol. 80, p. 1339.
Jang et al., "Processing of Nano Graphene Platelets (NGPs) and NGP Nanocomposites: A Review" J. Materials Sci. (2008) vol. 43, pp. 5092-5101.
Ji et al., "A highly ordered nanostructured carbon—sulphur cathode for lithium—sulphur batteries" Nature Materials (2009) vol. 8, pp. 500-506.
JP 61275116 Dec. 5, 1986.
Katsumi et al., "Evaluation of stacking nanostructure in soil humic acids by analysis of the 002 band of their X-ray diffraction profiles" Soil Science and Plant Nutrition (2015) vol. 61, No. 4, pp. 603-612.
PCT/US17/18708 International Search Report and Written Opinion dated Jun. 6, 2017, 12 pages.
PCT/US17/36032 International Search Report and Written Opinion dated Aug. 25, 2017, 11 pages.
PCT/US17/43284 International Search Report and Written Opinion dated Oct. 12, 2017, 7 pages.
PCT/US17/43485 International Search Report and Written Opinion dated Sep. 27, 2017, 10 pages.

\* cited by examiner

20 μm (50 μm wide)

HUMIC ACID-BONDED METAL FOIL FILM CURRENT COLLECTOR AND BATTERY AND SUPERCAPACITOR CONTAINING SAME

CROSS REFERENCE TO RELATED APPLICATIONS

The present application is a divisional of U.S. patent application Ser. No. 15/243,606 filed Aug. 22, 2016, the contents of which are hereby incorporated by reference for all purposes.

FIELD

The present disclosure provides a current collector for a lithium battery or supercapacitor. The current collector is a metal foil bonded with a thin film of highly oriented humic acid or humic acid-derived highly conducting graphitic film.

BACKGROUND

This patent application is directed at a current collector that works with an anode electrode (anode active material layer) or a cathode electrode (cathode active material layer) of a lithium cell (e.g. lithium-ion cell, lithium-metal cell, or lithium-ion capacitor), a supercapacitor, a non-lithium battery (such as the zinc-air cell, nickel metal hydride battery, sodium-ion cell, and magnesium-ion cell), and other electrochemical energy storage cells. This application is not part of the anode active material layer or the cathode active material layer per se.

The lithium-metal cell includes the conventional lithium-metal rechargeable cell (e.g. using a lithium foil as the anode and $MnO_2$ particles as the cathode active material), lithium-air cell (Li-Air), lithium-sulfur cell (Li—S), and the emerging lithium-graphene cell (Li-graphene, using graphene sheets as a cathode active material), lithium-carbon nanotube cell (Li-CNT, using CNTs as a cathode), and lithium-nano carbon cell (Li—C, using nano carbon fibers or other nano carbon materials as a cathode). The anode and/or the cathode active material layer can contain some lithium, or can be prelithiated prior to or immediately after cell assembly.

Rechargeable lithium-ion (Li-ion), lithium metal, lithium-sulfur, and Li metal-air batteries are considered promising power sources for electric vehicle (EV), hybrid electric vehicle (HEV), and portable electronic devices, such as lap-top computers and mobile phones. Lithium as a metal element has the highest lithium storage capacity (3,861 mAh/g) compared to any other metal or metal-intercalated compound as an anode active material (except $Li_{4.4}Si$, which has a specific capacity of 4,200 mAh/g). Hence, in general, Li metal batteries (having a lithium metal anode) have a significantly higher energy density than conventional lithium-ion batteries (having a graphite anode).

Historically, rechargeable lithium metal batteries were produced using non-lithiated compounds having relatively high specific capacities, such as $TiS_2$, $MoS_2$, $MnO_2$, $CoO_2$, and $V_2O_5$, as the cathode active materials, which were coupled with a lithium metal anode. When the battery was discharged, lithium ions were transferred from the lithium metal anode to the cathode through the electrolyte and the cathode became lithiated. Unfortunately, upon repeated charges and discharges, the lithium metal resulted in the formation of dendrites at the anode that ultimately caused internal shorting, thermal runaway, and explosion. As a result of a series of accidents associated with this problem, the production of these types of secondary batteries was stopped in the early 1990's giving ways to lithium-ion batteries. Even now, cycling stability and safety concerns remain the primary factors preventing the further commercialization of Li metal batteries (e.g. Lithium-sulfur and Lithium-transition metal oxide cells) for EV, HEV, and microelectronic device applications.

Prompted by the aforementioned concerns over the safety of earlier lithium metal secondary batteries led to the development of lithium-ion secondary batteries, in which pure lithium metal sheet or film was replaced by carbonaceous materials (e.g. natural graphite particles) as the anode active material. The carbonaceous material absorbs lithium (through intercalation of lithium ions or atoms between graphene planes, for instance) and desorbs lithium ions during the re-charge and discharge phases, respectively, of the lithium-ion battery operation. The carbonaceous material may comprise primarily graphite that can be intercalated with lithium and the resulting graphite intercalation compound may be expressed as $Li_xC_6$, where x is typically less than 1 (with graphite specific capacity <372 mAh/g).

Although lithium-ion (Li-ion) batteries are promising energy storage devices for electric drive vehicles, state-of-the-art Li-ion batteries have yet to meet the cost, safety, and performance targets (such as high specific energy, high energy density, good cycle stability, and long cycle life). Li-ion cells typically use a lithium transition-metal oxide or phosphate as a positive electrode (cathode) that de/re-intercalates Li at a high potential with respect to the carbon negative electrode (anode). The specific capacity of lithium transition-metal oxide or phosphate based cathode active material is typically in the range from 140-170 mAh/g. As a result, the specific energy (gravimetric energy density) of commercially available Li-ion cells featuring a graphite anode and a lithium transition-metal oxide or phosphate based cathode is typically in the range from 120-220 Wh/kg, most typically 150-200 Wh/kg. The corresponding typical range of energy density (volumetric energy density) is from 400 to 550 Wh/L. The energy densities are even lower under high charge-discharge rate conditions. These specific energy values are two to three times lower than what would be required if battery-powered electric vehicles are to be widely accepted.

A typical battery cell is composed of (a) an anode current collector, (b) an anode electrode (also referred to as the anode active material layer, typically including an anode active material, a conductive filler, and a binder resin component) bonded to the anode current collector with a binder resin, (c) an electrolyte/separator, (d) a cathode electrode (also referred to as the cathode active material layer, typically including a cathode active material, a conductive filler, and a binder resin), (e) a cathode current collector bonded to the cathode electrode with a binder resin, (f) metal tabs that are connected to external wiring, and (g) casing that wraps around all other components except for the tabs.

Current collectors, typically aluminum foil (at the cathode) and copper foil (at the anode), account for about 15-20% by weight and 10-15% by cost of a lithium-ion battery. Therefore, thinner, lighter foils would be preferred. However, there are several major issues associated with state-of-the-art current collectors: (a) Due to easy creasing and tearing, thinner foils tend to be more expensive and harder to work with; (b) Current collectors must be electrochemically stable with respect to the cell components over the operating potential window of the electrode. In practice, continued corrosion of the current collectors mainly by the electrolyte can lead to a gradual increase in the internal resistance of the battery, resulting in persistent loss of the apparent capacity or poor cycling life: (c) Oxidation of metal current collectors is a strong exothermic reaction that can significantly contribute to thermal runaway of a lithium battery.

Accordingly, the current collectors are crucially important for cost, weight, safety, and performance of a battery. Instead of metals, graphene or graphene-coated solid metal or plastic has been considered as a potential current collector material, as summarized in the references listed below:

1. Li Wang, Xiangming He, Jianjun Li, Jian Gao, Mou Fang, Guangyu Tian, Jianlong Wang, Shoushan Fan, "Graphene-coated plastic film as current collector for lithium/sulfur batteries," J. Power Source, 239 (2013) 623-627.
2. S. J. Richard Prabakar, Yun-Hwa Hwang, Eun Gyoung Bae, Dong Kyu Lee, Myoungho Pyo, "Graphene oxide as a corrosion inhibitor for the aluminum current collector in lithium ion batteries," Carbon, 52 (2013) 128-136.
3. Yang Li, et al. Chinese Patent Pub. No. CN 104600320 A (2015, May, 6).
4. Zhaoping Liu, et al (Ningbo Institute of Materials and Energy, China), WO 2012/151880 A1 (Nov. 15, 2012).
5. Gwon, H.; Kim, H-S; Lee, K E; Seo, D-H; Park, Y C; Lee, Y-S; Ahn, B T; Kang, K "Flexible energy storage devices based on graphene paper," *Energy and Environmental Science.* 4 (2011) 1277-1283.
6. Ramesh C. Bhardwaj and Richard M. Mank, "Graphene current collectors in batteries for portable electronic devices," US 20130095389 A1, Apr. 18, 2013.

Currently, graphene current collectors come in three different forms: graphene-coated substrate [Ref. 1-4], free-standing graphene paper [Ref. 5], and monolayer graphene film produced by transition metal (Ni, Cu)-catalyzed chemical vapor deposition (CVD) followed by metal etching [Ref. 6].

In the preparation of graphene-coated substrate, small isolated sheets or platelets of graphene oxide (GO) or reduced graphene oxide (RGO) are spray-deposited onto a solid substrate (e.g. plastic film or Al foil). In the graphene layer, the building blocks are separated graphene sheets/platelets (typically 0.5-5 μm in length/width and 0.34-30 nm in thickness) that are typically bonded by a binder resin, such as PVDF [Refs. 1, 3, and 4]. Although individual graphene sheets/platelets can have a relatively high electrical conductivity (within the confine of that 0.5-5 μm), the resulting graphene-binder resin composite layer is relatively poor in electrical conductivity (typically <100 S/cm and more typically <10 S/cm). Furthermore, another purpose of using a binder resin is to bond the graphene-binder composite layer to the substrate (e.g. Cu foil); this implies that there is a binder resin (adhesive) layer between Cu foil and the graphene-binder composite layer. Unfortunately, this binder resin layer is electrically insulating and the resulting detrimental effect seems to have been totally overlooked by prior workers.

Although Prabakar, et al. [Ref. 2] does not seem to have used a binder resin in forming an aluminum foil coated with discrete graphene oxide sheets, this graphene oxide-coated Al foil has its own problem. It is well-known in the art that aluminum oxide ($Al_2O_3$) readily forms on surfaces of an aluminum foil and cleaning with acetone or alcohol is not capable of removing this passivating layer of aluminum oxide or alumina. This aluminum oxide layer is not only electrically and thermally insulating, but actually is not resistant to certain types of electrolyte. For instance, the most commonly used lithium-ion battery electrolyte is $LiPF_6$ dissolved in an organic solvent. A trace amount of $H_2O$ in this electrolyte can trigger a series of chemical reactions that involve formation of HF (a highly corrosive acid) that readily breaks up the aluminum oxide layer and continues to corrode the Al foil and consume electrolyte. The capacity decay typically becomes much apparent after 200-300 charge-discharge cycles.

Free-standing graphene paper is typically prepared by vacuum-assisted filtration of GO or RGO sheets/platelets suspended in water. In a free-standing paper, the building blocks are separated graphene sheets/platelets that are loosely overlapped together. Again, although individual graphene sheets/platelets can have a relatively high electrical conductivity (within the confine of that 0.5-5 μm), the resulting graphene paper has a very low electrical conductivity; e.g. 8,000 S/m or 80 S/cm [Ref. 5], which is 4 orders of magnitude lower than the conductivity of Cu foil ($8 \times 10^5$ S/cm).

There are several major problems associated with the most commonly used process for producing graphene (i.e. the chemical oxidation/intercalation process):

(1) The process requires the use of large quantities of several undesirable chemicals, such as sulfuric acid, nitric acid, and potassium permanganate or/and sodium chlorate.
(2) The thermal exfoliation requires a high temperature (typically 800-1,050° C.) and, hence, is a highly energy-intensive process.
(3) The approach requires a very tedious washing and purification step. For instance, typically 2.5 kg of water is used to wash and recover 1 gram of GIC, producing huge quantities of waste water that need to be properly treated.
(4) The resulting products are graphene oxide (GO) platelets that must undergo a further chemical reduction treatment to reduce the oxygen content. Typically even after reduction, the electrical conductivity of GO platelets remains much lower than that of pristine graphene. Furthermore, the reduction procedure often involves the utilization of toxic chemicals, such as hydrazine.
(5) Furthermore, the quantity of intercalation solution retained on the flakes after draining may range from 20 to 150 parts of solution by weight per 100 parts by weight of graphite flakes (pph) and more typically about 50 to 120 pph. During the high-temperature exfoliation, the residual intercalant species retained by the flakes decompose to produce various species of sulfuric and nitrous compounds (e.g., $NO_x$ and $SO_x$), which are undesirable. The effluents require expensive remediation procedures in order not to have an adverse environmental impact.

The catalyzed CVD process for graphene production involves introduction of a hydrocarbon gas into a vacuum chamber at a temperature of 500-800° C. Under these stringent conditions, the hydrocarbon gas gets decomposed with the decomposition reaction being catalyzed by the transition metal substrate (Ni or Cu). The Cu/Ni substrate is then chemically etched away using a strong acid, which is not an environmentally benign procedure. The whole process is slow, tedious, and energy-intensive, and the resulting graphene is typically a single layer graphene or few-layer graphene (up to 5 layers maximum since the underlying Cu/Ni layer loses its effectiveness as a catalyst).

Bhardwaj, et al [Ref. 6] suggested stacking multiple CVD-graphene films to a thickness of 1 μm or a few μm; however, this would require hundreds or thousands of films stacked together (each film being typically 0.34 nm to 2 nm thick). Although Bhardwaj, et al claimed that "The graphene may reduce the manufacturing cost and/or increase the energy density of a battery cell," no experimental data was presented to support their claim. Contrary to this claim, the CVD graphene is a notoriously expensive process and even a single-layer of CVD graphene film would be significantly more expensive than a sheet of Cu or Al foil given the same area (e.g. the same 5 cm×5 cm). A stack of hundreds or thousands of mono-layer or few-layer graphene films as suggested by Bhardwaj, et al would mean hundreds or thousands times more expensive than a Cu foil current collector. This cost would be prohibitively high. Further, the high contact resistance between hundreds of CVD graphene films in a stack and the relatively low conductivity of CVD graphene would lead to an overall high internal resistance, nullifying any potential benefit of using thinner films (1 µm of graphene stack vs. 10 µm of Cu foil) to reduce the overall cell weight and volume. It seems that the patent application of Bhardwaj, et al [Ref. 6], containing no data whatsoever, is nothing but a concept paper.

The above discussions have clearly shown that all three forms of the graphene-enhanced or graphene-based current collector do not meet the performance and cost requirements for use in a battery or supercapacitor. A strong need exists for a different type of material for use as a current collector.

The present disclosure is directed at a new class of materials, herein referred to as a highly oriented film of humic acid (HA), alone or in combination with graphene, which is chemically bonded to metal foil surface. Graphene used herein includes pristine graphene, graphene oxide, graphene fluoride, nitrogenated graphene, hydrogenated graphene, boron-doped graphene, any other type of doped graphene, and other type of chemically functionalized graphene. Quite unexpectedly and significantly, this highly oriented film of HA or HA/graphene mixture can be thermally converted to a highly conducting graphitic film.

Humic acid (HA) is an organic matter commonly found in soil and can be extracted from the soil using a base (e.g. KOH). HA can also be extracted, with a high yield, from a type of coal called leonardite, which is a highly oxidized version of lignite coal. HA extracted from leonardite contains a number of oxygenated groups (e.g. carboxyl groups) located around the edges of the graphene-like molecular center ($SP^2$ core of hexagonal carbon structure). This material is slightly similar to graphene oxide (GO) which is produced by strong acid oxidation of natural graphite. HA has a typical oxygen content of 5% to 42% by weight (other major elements being carbon and hydrogen). HA, after chemical or thermal reduction, has an oxygen content of 0.01% to 5% by weight. For claim definition purposes in the instant application, humic acid (HA) refers to the entire oxygen content range, from 0.01% to 42% by weight. The reduced humic acid (RHA) is a special type of HA that has an oxygen content of 0.01% to 5% by weight.

It is surprising to discover that humic acid, when brought in intimate contact with a surface of a metal foil, can chemically bond to the metal foil. It is further surprising to discover that, when properly aligned and packed together, humic acid molecules can chemically link with one another to obtain longer and wider humic acid sheets. These humic acid molecules are also capable of chemically linking or bonding with graphene sheets, if present and properly aligned and packed. The resulting humic acid- or graphitic film-bonded thin metal foil is electrolyte-compatible, non-reactive, corrosion-protective, of low contact resistance, thermally and electrically conductive, ultra-thin, and lightweight, enabling a battery or capacitor to deliver a higher output voltage, higher energy density, high rate-capability, and much longer cycle life.

SUMMARY

The present disclosure provides a highly oriented humic acid-bonded metal foil current collector for use in a battery or supercapacitor. The disclosure also provides a current collector composed of a metal foil and a humic acid-derived highly conducting graphitic film bonded to one or two primary surfaces of the metal foil. The disclosure also provides processes for producing these current collectors.

The invented current collector comprises: (a) a thin metal foil having a thickness from 1 µm to 30 µm (preferably from 4 µm to 12 µm) and two opposed but substantially parallel primary surfaces; and (b) at least one thin film of highly oriented humic acid (HA) or a mixture of HA and graphene sheets (or a highly conducting graphitic film derived from this thin film) being chemically bonded to at least one of the two opposed primary surfaces of the metal foil. The thin film of HA or HA/graphene mixture or the derived graphitic film has a thickness from 10 nm to 10 µm, an oxygen content from 0.01% to 10% by weight, a physical density from 1.3 to 2.2 g/cm$^3$, hexagonal carbon planes being oriented substantially parallel to each other and parallel to the primary surfaces, an inter-planar spacing of 0.335 to 0.50 nm between hexagonal carbon planes, a thermal conductivity greater than 250 W/mK (more typically >500 W/mK), and an electrical conductivity greater than 800 S/cm (more typically >1,500 S/cm) when measured alone without said thin metal foil.

Preferably, each of the two opposed primary surfaces is chemically bonded with such a thin film of humic acid or HA/graphene mixture or a graphitic film derived from this thin film produced through heat treatments. Also preferably, one or both thin films of HA or both HA and graphene (or the derived graphitic film) are chemically bonded to one or both opposed primary surfaces of the metal foil without using a binder or adhesive. If a binder is used, this binder is an electrically conductive material selected from an intrinsically conductive polymer, pitch, amorphous carbon, or carbonized resin (polymeric carbon). Preferably, the thin metal foil has a thickness from 4 to 12 µm. Also preferably, the thin film of humic acid or HA/graphene mixture or the graphitic film has a thickness from 20 nm to 2 µm.

For the current collector, preferably the metal foil is selected from Cu, Ti, Ni, stainless steel, Al foil, or a combination thereof. Preferably, the primary surface does not contain a layer of passivating metal oxide thereon (e.g. no alumina, $Al_2O_3$, on Al foil surface).

Preferably, the thin film of HA or HA/graphene mixture or the graphitic film derived therefrom has an oxygen content from 1% to 5% by weight. Further preferably, the thin film or the graphitic film derived therefrom has an oxygen content less than 1%, an inter-planar spacing less than 0.345 nm, and an electrical conductivity no less than 3,000 S/cm. More preferably, the thin film or the graphitic film derived therefrom has an oxygen content less than 0.1%, an inter-planar spacing less than 0.337 nm, and an electrical conductivity no less than 5,000 S/cm. Still more preferably, the thin film or the graphitic film derived therefrom has an oxygen content no greater than 0.05%, an inter-planar spacing less than 0.336 nm, a mosaic spread value no greater than 0.7, and an electrical conductivity no less than 8,000 S/cm. Even more preferably, the thin film or the graphitic film derived therefrom has an inter-planar spacing less than 0.336 nm, a mosaic spread value no greater than 0.4, and an electrical conductivity greater than 10,000 S/cm.

More preferably, the thin film of HA or HA/graphene mixture or the graphitic film derived therefrom exhibits an inter-planar spacing less than 0.337 nm and a mosaic spread value less than 1.0. Most preferably, the thin film e or the graphitic film derived therefrom exhibits a degree of graphitization no less than 80% and/or a mosaic spread value no greater than 0.4.

In certain embodiments, the thin film of HA or HA/graphene mixture is obtained by depositing a suspension of HA or a mixture of HA and graphene sheets onto said at least one primary surface under the influence of an orientation-controlling stress to form a layer of HA or a mixture of HA and graphene sheets and then heat-treating said layer at a heat treatment temperature from 80° C. to 1,500° C. More preferably, the heat treatment temperature is from 80° C. to 500° C. and further more preferably from 80° C. to 200° C.

The highly oriented thin film of HA or HA/graphene or the graphitic film derived therefrom bonded to the underlying current collector typically contains chemically bonded humic acid molecules or chemically merged humic acid and graphene planes that are parallel to one another. Preferably, the thin film is a continuous length film having a length no less than 5 cm and a width no less than 1 cm and this thin film is made by a roll-to-roll process.

Preferably, the thin film of HA or HA/graphene mixture or the graphitic film derived therefrom, when measured alone (as a free-standing layer without the presence of a metal foil), has a physical density greater than 1.6 g/cm3, and/or a tensile strength greater than 30 MPa. More preferably, the thin film or the graphitic film derived therefrom, when measured alone, has a physical density greater than 1.8 g/cm3, and/or a tensile strength greater than 50 MPa. Most preferably, the thin film or the graphitic film derived therefrom, when measured alone, has a physical density greater than 2.0 g/cm$^3$, and/or a tensile strength greater than 80 MPa.

The present disclosure also provides a rechargeable lithium battery or lithium-ion battery containing the presently invented current collector as an anode current collector and/or a cathode current collector. The rechargeable lithium battery may be a lithium-sulfur cell, a lithium-selenium cell, a lithium sulfur/selenium cell, a lithium-air cell, a lithium-graphene cell, or a lithium-carbon cell.

The present disclosure also provides a capacitor containing the invented current collector as an anode current collector or a cathode current collector, which capacitor is a symmetric ultracapacitor, an asymmetric ultracapacitor cell, a hybrid supercapacitor-battery cell, or a lithium-ion capacitor cell.

The disclosure also provides a process for producing a highly oriented humic acid film-bonded metal foil current collector for use in a battery or supercapacitor. The process comprises:
(a) preparing a dispersion of humic acid (HA) or chemically functionalized humic acid (CHA) sheets dispersed in a liquid medium, wherein the HA sheets contain an oxygen content higher than 5% by weight or the CHA sheets contain non-carbon element content higher than 5% by weight;
(b) dispensing and depositing the HA or CHA dispersion onto at least one primary surface of a metal foil to form a wet layer of HA or CHA on the surface, wherein the dispensing and depositing procedure includes subjecting the dispersion to an orientation-inducing stress;
(c) partially or completely removing the liquid medium from the wet layer of HA or CHA to form a dried HA or CHA layer having hexagonal carbon planes and an inter-planar spacing $d_{002}$ of 0.4 nm to 1.3 nm as determined by X-ray diffraction; and
(d) heat-treating the dried HA or CHA layer at a first heat treatment temperature higher than 80° C. for a sufficient period of time to produce the highly oriented humic acid film-bonded metal foil current collector wherein the fumic acid film contains inter-connected, merged or thermally reduced HA or CHA sheets that are substantially parallel to each other and are chemically bonded and parallel to the primary surface and the humic acid film has a physical density no less than 1.3 g/cm$^3$, a thermal conductivity of at least 250 W/mK, and/or an electrical conductivity no less than 500 S/cm. The process may further comprise a step of compressing the humic acid film of merged or reduced HA or CHA after said step (d).

The process may comprise an additional step (e) of further heat-treating the humic acid film-bonded metal foil at a second heat treatment temperature higher than the first heat treatment temperature for a sufficient period of time to produce a graphitic film-bonded metal foil current collector, wherein the graphitic film has an inter-planar spacing $d_{002}$ less than 0.4 nm and an oxygen content or non-carbon element content less than 5% by weight; and (f) compressing the graphitic film to produce a highly conducting graphitic film having a physical density no less than 1.3 g/cm$^3$, a thermal conductivity of at least 500 W/mK, and/or an electrical conductivity no less than 1,000 S/cm. The highly conductive graphitic film preferably has a thickness from 5 nm to 20 μm, but more preferably from 10 nm to 2 μm.

The HA or CHA dispersion may further contain graphene sheets or molecules dispersed therein and the HA-to-graphene or CHA-to-graphene ratio is from 1/100 to 100/1 wherein the graphene is selected from pristine graphene, graphene oxide, reduced graphene oxide, graphene fluoride, graphene bromide, graphene iodide, boron-doped graphene, nitrogen-doped graphene, chemically functionalized graphene, or a combination thereof. The process may include additional step (e) of further heat-treating the humic acid film of merged or reduced HA or CHA at a second heat treatment temperature higher than the first heat treatment temperature for a sufficient period of time to produce a graphitic film having an inter-planar spacing $d_{002}$ less than 0.4 nm and an oxygen content or non-carbon element content less than 5% by weight; and step (f) of compressing the graphitic film to produce a highly conducting graphitic film having a physical density no less than 1.6 g/cm$^3$, a thermal conductivity of at least 700 W/mK, and/or an electrical conductivity no less than 1,500 S/cm.

In certain embodiments, the HA or CHA sheets are in an amount sufficient to form a liquid crystal phase in the liquid medium. Preferably, the dispersion contains a first volume fraction of HA or CHA dispersed in the liquid medium that exceeds a critical volume fraction ($V_c$) for a liquid crystal phase formation and the dispersion is concentrated to reach a second volume fraction of HA or CHA, greater than the first volume fraction, to improve a HA or CHA sheet orientation. Preferably, the first volume fraction is equivalent to a weight fraction of from 0.05% to 3.0% by weight of HA or CHA in the dispersion. The dispersion may be concentrated to contain higher than 3.0% but less than 15% by weight of HA or CHA dispersed in the liquid medium prior to said step (b).

In some embodiments, the dispersion further contains a polymer dissolved in said liquid medium or attached to HA or CHA.

The CHA may contain a chemical functional group selected from a polymer, $SO_3H$, COOH, $NH_2$, OH, R'CHOH, CHO, CN, COCl, halide, COSH, SH, COOR', SR', $SiR'_3$, $Si(-OR'-)_yR'_3$-y, $Si(-O-SiR'_2-)OR'$, R", Li, $AlR'_2$, Hg—X, $TlZ_2$ and Mg—X; wherein y is an integer equal to or less than 3, R' is hydrogen, alkyl, aryl, cycloalkyl, or aralkyl, cycloaryl, or poly(alkylether), R" is fluoroalkyl, fluoroaryl, fluorocycloalkyl, fluoroaralkyl or cycloaryl, X is halide, and Z is carboxylate or trifluoroacetate, or a combination thereof.

The graphene sheets, if present, may contain chemically functionalized graphene containing a chemical functional group selected from a polymer, $SO_3H$, COOH, $NH_2$, OH, R'CHOH, CHO, CN, COCl, halide, COSH, SH, COOR', SR', $SiR'_3$, $Si(-OR'-)_yR'_3$-y, $Si(-O-SiR'_2-)OR'$, R", Li, $AlR'_2$, Hg—X, $TlZ_2$ and Mg—X; wherein y is an integer equal to or less than 3, R' is hydrogen, alkyl, aryl, cycloalkyl, or aralkyl, cycloaryl, or poly(alkylether), R" is fluoroalkyl, fluoroaryl, fluorocycloalkyl, fluoroaralkyl or cycloaryl, X is halide, and Z is carboxylate or trifluoroacetate, or a combination thereof.

Preferably, the liquid medium consists of water or a mixture of water and an alcohol. Alternatively, the liquid medium contains a non-aqueous solvent selected from polyethylene glycol, ethylene glycol, propylene glycol, an alcohol, a sugar alcohol, a polyglycerol, a glycol ether, an amine based solvent, an amide based solvent, an alkylene carbonate, an organic acid, or an inorganic acid.

The second heat treatment temperature may be higher than 1,500° C. for a length of time sufficient for decreasing an inter-plane spacing $d_{002}$ to a value less than 0.36 nm and decreasing the oxygen content or non-carbon element content to less than 0.1% by weight. Specifically, the second heat treatment temperature may be from 1,500° C. to 3,200° C.

The process is preferably a roll-to-roll or reel-to-reel process, wherein step (b) includes feeding a sheet of the metal foil from a roller to a deposition zone, depositing a layer of HA or CHA dispersion onto at least one primary surface of the metal foil to form a wet layer of HA or CHA dispersion thereon, drying the HA or CHA dispersion to form a dried HA or CHA layer deposited on metal foil surface, and collecting the HA or CHA layer-deposited metal foil on a collector roller.

In certain embodiments, the first heat treatment temperature contains a temperature in the range from 100° C.-1,500° C. and the highly oriented humic acid film has an oxygen content less than 2.0%, an inter-planar spacing less than 0.35 nm, a physical density no less than 1.6 g/cm³, a thermal conductivity of at least 800 W/mK, and/or an electrical conductivity no less than 2,500 S/cm. In other embodiments, the first heat treatment temperature contains a temperature in the range from 1,500° C.-2,100° C. and the highly oriented humic acid film, becoming a highly conducting graphitic film, has an oxygen content less than 1.0%, an inter-planar spacing less than 0.345 nm, a thermal conductivity of at least 1,000 W/mK, and/or an electrical conductivity no less than 5,000 S/cm.

In some embodiments, the first and/or second heat treatment temperature contains a temperature greater than 2,100° C. and the highly conducting graphitic film has an oxygen content no greater than 0.1%, an inter-graphene spacing less than 0.340 nm, a mosaic spread value no greater than 0.7, a thermal conductivity of at least 1,300 W/mK, and/or an electrical conductivity no less than 8,000 S/cm. If the second heat treatment temperature contains a temperature no less than 2,500° C., the highly conducting graphitic film has an inter-graphene spacing less than 0.336 nm, a mosaic spread value no greater than 0.4, a thermal conductivity greater than 1,500 W/mK, and/or an electrical conductivity greater than 10,000 S/cm. The degree of graphitization may be no less than 80% and a mosaic spread value less than 0.4.

Typically, the HA or CHA sheets have a maximum original length and the highly oriented humic acid film contains HA or CHA sheets having a length larger than the maximum original length. This implies that some humic acid molecules have merged with other HA molecules in an edge-to-edge manner to increase the length or width of the planar molecules or sheets. The step (e) of heat-treating induces chemical linking, merging, or chemical bonding of HA or CHA sheets with other HA or CHA sheets, or with graphene sheets to form a graphitic structure. The highly conducting graphitic film is a poly-crystal graphene structure having a preferred crystalline orientation as determined by said X-ray diffraction method.

The process typically results in the formation of a highly oriented graphitic film having an electrical conductivity greater than 5,000 S/cm, a thermal conductivity greater than 800 W/mK, a physical density greater than 1.9 g/cm³, a tensile strength greater than 80 MPa, and/or an elastic modulus greater than 60 GPa. Further typically, the highly oriented graphitic film has an electrical conductivity greater than 8,000 S/cm, a thermal conductivity greater than 1,200 W/mK, a physical density greater than 2.0 g/cm³, a tensile strength greater than 100 MPa, and/or an elastic modulus greater than 80 GPa. With a final heat treatment temperature (the first or second heat treatment temperature) higher than 1,500° C., the highly oriented graphitic film has an electrical conductivity greater than 12,000 S/cm, a thermal conductivity greater than 1,500 W/mK, a physical density greater than 2.1 g/cm³, a tensile strength greater than 120 MPa, and/or an elastic modulus greater than 120 GPa.

DETAILED DESCRIPTION OF PREFERRED EMBODIMENTS

Figure 1A:
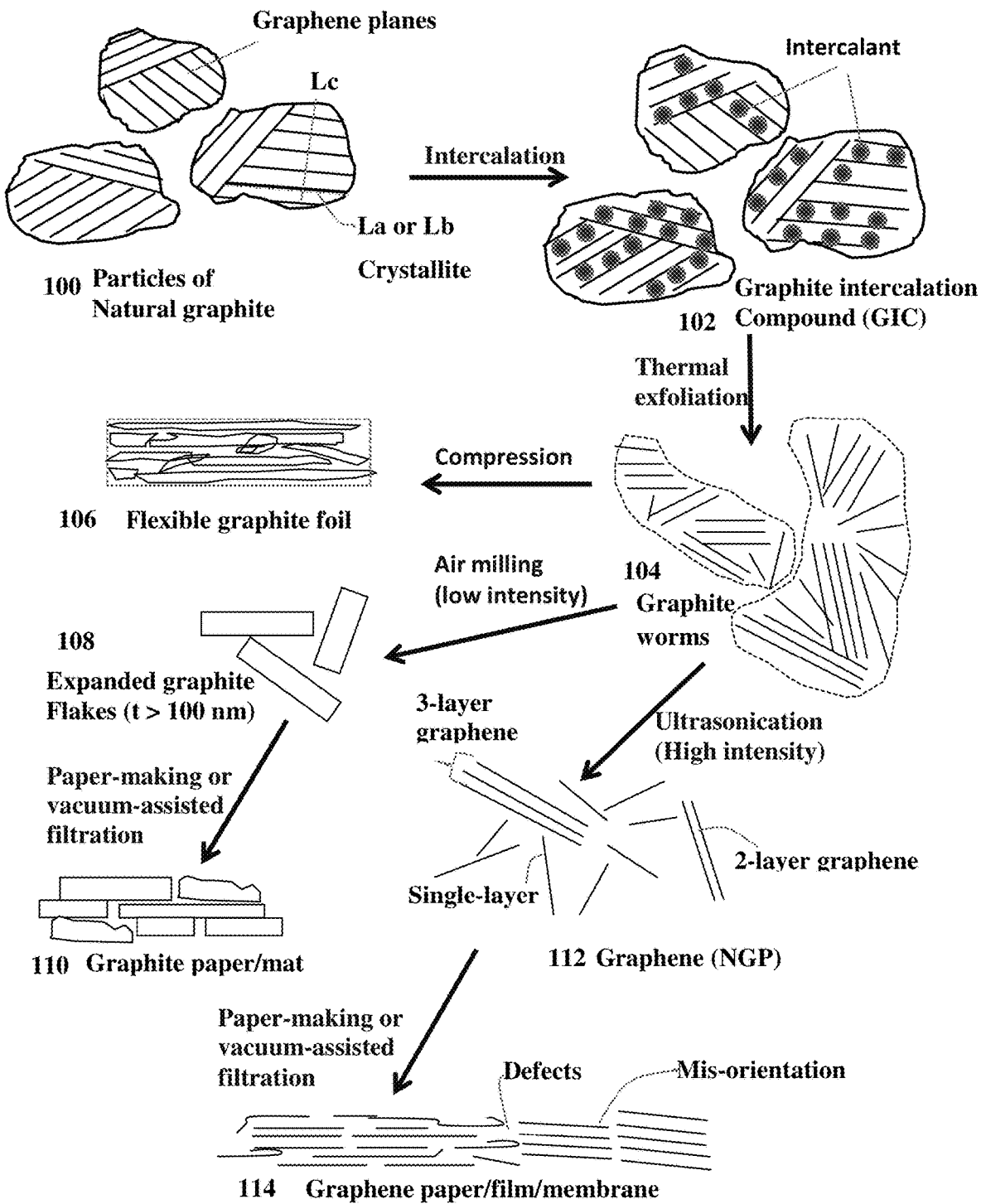
FIG. 1(A) A flow chart illustrating various prior art processes for producing exfoliated graphite products (flexible graphite foils and flexible graphite composites) and pyrolytic graphite (bottom portion), along with a process for producing isolated graphene sheets and aggregates of graphene or graphene oxide sheets in the form of a graphene paper or membrane.
Figure 1B:
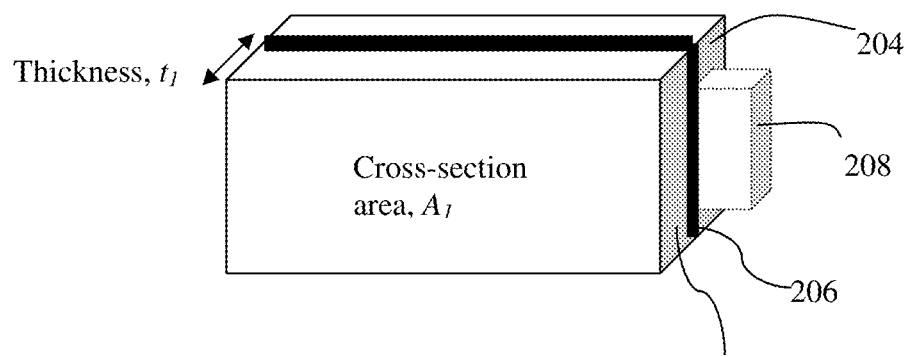
FIG. 1(B) The prior art graphene-coated metal foil current collector with a binder resin layer between the graphene layer (a graphene-resin composite) and the metal foil (e.g. Cu foil).
Figure 1C:
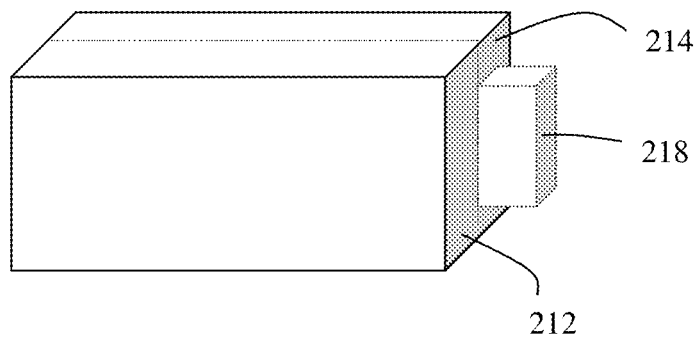
FIG. 1(C) A free-standing, non-supported thin metal foil with one primary surface of the metal foil being bonded with a thin film of HA or HA/graphene mixture.

The present disclosure provides a humic acid-bonded metal foil thin-film current collector (e.g. as schematically shown in FIG. 1(C)) for use in a battery or supercapacitor. In a preferred embodiment, the current collector comprises: (a) a free-standing, non-supported thin metal foil (214 in FIG. 1(C)) having a thickness from 1 µm to 30 µm and two opposed but substantially parallel primary surfaces; and (b) a thin film 212 of humic acid (HA) or HA/graphene mixture chemically bonded to at least one of the two opposed primary surfaces (without using a binder or adhesive). FIG. 1(C) only shows one primary surface of the metal foil 214 being bonded with a thin film 212 of HA or HA/graphene mixture. However, preferably, the opposite primary surface is also bonded with a thin film of HA or HA/graphene mixture (not shown in FIG. 1(C)). As a terminal pole for electrically connecting the battery/supercapacitor to an external circuit, a metal tab 218 is typically welded or soldered to the metal foil 214.

As illustrated in FIG. 1(C), a preferred embodiment of the present disclosure is a HA-bonded metal foil current collector, wherein no binder resin layer or passivating aluminum oxide layer is present between the film of HA or HA/graphene mixture and the Cu foil or Al foil. In contrast, as schematically illustrated in FIG. 1(B), the prior art graphene-coated metal foil current collector typically and necessarily requires a binder resin layer between the graphene layer (a graphene-resin composite) and the metal foil (e.g. Cu foil). In the case of prior art graphene-coated Al foil [Prabakar et al.; Ref. 2], a passivating aluminum oxide (alumina) layer is naturally present between the graphene layer and the Al metal foil. This is due to the well-known fact that aluminum foil, upon fabrication and exposure to room air, always forms a passivating aluminum oxide layer on the surfaces of the Al foil. Simple cleaning by acetone or alcohol is incapable of removing this alumina layer. As will be demonstrated in later paragraphs, the presence of a layer of binder resin or aluminum oxide, even as thin as just 1 nm, has an enormous effect on increasing the contact resistance between the graphene layer and the metal foil. This surprising discovery by us has been totally overlooked by all prior art workers and, hence, prior art graphene-coated metal foils have not met the performance and cost requirements of a lithium battery or supercapacitor current collector.

A very significant and unexpected advantage of bringing humic acid sheets in direct contact with the primary surfaces of a Cu, Ni, steel, or Ti foil is the notion that HA molecules can be well-bonded to these metal foils under the presently invented processing conditions, without using an external resin binder or adhesive (hence, no dramatically increased contact resistance). These processing conditions include well-aligning HA (or a mixture of HA and graphene) molecules or sheets on the metal foil surface and then heat-treating the two-layer structure at a temperature in the range from 80° C.-1,500° C. (more typically and desirably of 80° C.-500° C., and most typically and desirably of 80° C.-200° C.). Optionally, but not preferably, the heat treatment temperature can be as high as 1,500-3,000° C. (provided the metal foil can withstand such a high temperature).

These processing conditions, in the cases of aluminum foil-based current collectors, preferably include chemically etching off the passivating aluminum oxide layer prior to being coated with and bonded by HA, followed by a heat treatment under comparable temperature conditions described above. Alternatively, the HA molecules may be prepared in an acidic state, which is characterized by having high oxygen contents, reflecting high amounts of —OH and —COOH groups and having a pH value less than 5.0 (preferably <3.0 and even more preferably <2.0). The Al foil may be allowed to get immersed in a bath of HA solution, wherein the acidic environment naturally removes the passivating $Al_2O_3$ layer. When the Al foil emerges from the bath, HA molecules or sheets naturally adhere to the clean, etched Al foil surfaces, effectively preventing the exposure of Al foil surfaces to open air (hence, no passivating $Al_2O_3$ layer and no added contact resistance between an Al foil surface and the HA layer). This strategy has never been previously disclosed or suggested.

In addition to the chemical bonding power of the presently invented HA layer and the chemical etching power of the HA solution, the resulting thin film of HA or HA/graphene mixture in the presently invented HA-bonded metal foil has a thickness from 10 nm to 10 µm, an oxygen content from 0.1% to 10% by weight, an inter-graphene plane spacing of 0.335 to 0.50 nm, a physical density from 1.3 to 2.2 g/cm$^3$, all HA and graphene sheets (if present) being oriented substantially parallel to each other and parallel to the primary surfaces, exhibiting a thermal conductivity greater than 500 W/mK, and/or electrical conductivity greater than 1,500 S/cm when measured alone without the thin metal foil. This thin film of HA or HA/graphene is chemically inert and provides a highly effective protective layer against corrosion of the underlying metal foil.

Now, let us take a closer look at the magnitude of the total resistance (including the contact resistance) in a three-layer structure as illustrated in FIG. 1(B). The electrons in the binder or passivating metal oxide layer may be viewed as a three-layer structure (FIG. 1(B)) with the graphene film, interfacial binder resin layer (or passivating alumina layer), and metal foil layer electrically connected in series.

The total resistance is the sum of the resistance values of the three layers: $R=R_1+R_2+R_3=\rho_1(t_1/A_1)+\rho_2(t_2/A_2)+\rho_3(t_3/A_3)=(1/\sigma_1)(t_1/A_1)+(1/a_2)(t_2/A_2)+(1/\sigma_3)(t_3/A_3)$, where $\rho$=resistivity, $\sigma$=conductivity, t=thickness, and A=area of a layer, and, approximately, $A_1=A_2=A_3$. Scanning electron microscopic examinations reveal that the binder resin or passivating alumina layers are typically 5-100 nm thick. The resistivity of most commonly used binder resin (PVDF) and that of alumina ($Al_2O_3$) are typically in the range from $10^{13}$-$10^{15}$ ohm-cm. Assume that $A_1=A_2=A_3=1$ cm$^2$, the thickness-direction resistivity $\rho_1$ of graphene layer=0.1 ohm-cm, the binder or alumina layer resistivity $\rho_2=1\times10^{14}$ ohm-cm and the metal foil layer resistivity is $\rho_3=1.7\times10^{-6}$ ohm-cm (Cu foil), or $\rho_3=2.7\times10^{-6}$ ohm-cm (Al foil). Also assume the optimum conditions where the Cu or Al foil thickness=6 µm, graphene layer thickness=1 µm, and the binder resin layer thickness is only 0.5 nm (actually it is from 5 nm to 100 nm). Then, the total resistance of the three-layer structure would be $5\times10^6$ ohm and the overall conductivity would be as low as $1.4\times10^{-10}$ S/cm (see first data row in Table 1 below). If we assume that the binder resin layer is 10 nm thick, the total resistance of the three-layer structure would be $1\times10^8$ ohm and the overall conductivity would be as low as $7.0\times10^{-12}$ S/cm (see 4th data row in Table 1 below). Such a 3-layer composite structure would not be a good current collector for a battery or supercapacitor since a high internal resistance would mean a low output voltage and high amount of internal heat generated. Similar results are observed for Ni, Ti, and stainless steel foil-based current collectors (data rows 7-10 of Table 1).

TABLE 1

| metal | $\rho_1$ ohm-cm | $t_1$ $10^{-4}$ cm | $A_1$ cm$^2$ | $\rho_2$ ohm-cm | $t_2$ $10^{-4}$ cm | $A_2$ cm$^2$ | $\rho_3$ ohm-cm | $t_3$ $10^{-4}$ cm | $A_3$ cm$^2$ | R ohm | $\sigma = t/(AR)$ S/cm |
|---|---|---|---|---|---|---|---|---|---|---|---|
| Cu | 0.1 | 1 | 1 | 1.00E+14 | 0.0005 | 1 | 1.70E−06 | 6 | 1 | 5.00E+06 | 1.40E−10 |
| Cu | 0.1 | 1 | 1 | 1.00E+14 | 0.001 | 1 | 1.70E−06 | 6 | 1 | 1.00E+07 | 7.00E−11 |
| Cu | 0.1 | 1 | 1 | 1.00E+14 | 0.005 | 1 | 1.70E−06 | 6 | 1 | 5.00E+07 | 1.40E−11 |
| Cu | 0.1 | 1 | 1 | 1.00E+14 | 0.01 | 1 | 1.70E−06 | 6 | 1 | 1.00E+08 | 7.01E−12 |
| Cu | 0.1 | 1 | 1 | 1.00E+14 | 0.001 | 1 | 1.70E−06 | 6 | 1 | 1.00E+07 | 7.00E−11 |
| Al | 0.1 | 1 | 1 | 1.00E+14 | 0.001 | 1 | 2.70E−06 | 6 | 1 | 1.00E+07 | 7.00E−11 |
| Ni | 0.1 | 1 | 1 | 1.00E+14 | 0.001 | 1 | 7.00E−06 | 6 | 1 | 1.00E+07 | 7.00E−11 |
| Ti | 0.1 | 1 | 1 | 1.00E+14 | 0.001 | 1 | 5.50E−05 | 6 | 1 | 1.00E+07 | 7.00E−11 |
| SS304 | 0.1 | 1 | 1 | 1.00E+14 | 0.001 | 1 | 7.20E−05 | 6 | 1 | 1.00E+07 | 7.00E−11 | graphene layer 202 (Layer 1) must move around in this layer, move across through the binder resin or passivating alumina layer 206 (Layer 2), and then move in the metal foil layer 204 (Layer 3) toward the terminal tab 208. For simplicity, we will consider only the total resistance against the electrons moving across the thickness of the graphene layer, the thickness of the binder/passivating layer, and the thickness of the metal foil layer. The electron movement in both the in-plane directions of graphene or metal foil is fast and of low resistance; hence, this resistance is neglected in the instant calculation.

The thickness-direction resistance of a sheet/film of conductor is given by R=(1/a) (t/A), where A=cross-section (length×width) of the conductor, t=thickness of the conductor, $\sigma$=conductivity=1/Q, and Q=resistivity, a material constant. A graphene-coated current collector containing a In contrast, if there is no binder resin or alumina layer ($t_2$=0), as is the case of the presently invented current collector, the total resistance of a graphene oxide-bonded Cu foil has a value of $1.0\times10^{-5}$ ohm (vs. $1.0\times10^{+7}$ ohm of a 3-layer structure containing a 1-µm binder resin layer). Please see Table 2 below. This represents a difference by 12 orders of magnitude (not 12-fold)! The conductivity would be $7.0\times10^{+1}$ S/cm for the instant 2-layer structure, in contrast to $7.0\times10^{-11}$ S/cm of the corresponding 3-layer structure. Again, the difference is by 12 orders of magnitude. Furthermore, we have discovered that the lithium batteries and supercapacitors featuring the presently invented graphene oxide-bonded metal foil current collectors always exhibit a higher voltage output, higher energy density, higher power density, more stable chare-discharge cycling response, and last longer without capacity decay or corrosion issues as compared to prior art graphene-based current collectors

TABLE 2

| metal | $\rho_1$ ohm-cm | $t_1$ $10^{-4}$ cm | $A_1$ cm$^2$ | $\rho_2$ ohm-cm | $t_2$ $10^{-4}$ cm | $A_2$ cm$^2$ | $\rho_3$ ohm-cm | $t_3$ $10^{-4}$ cm | $A_3$ cm$^2$ | R ohm | $\sigma = t/(AR)$ S/cm |
|---|---|---|---|---|---|---|---|---|---|---|---|
| Cu | 0.1 | 1 | 1 | 1.00E+14 | 0 | 1 | 1.70E−06 | 6 | 1 | 1.00E−05 | 7.00E+01 |
| Al | 0.1 | 1 | 1 | 1.00E+14 | 0 | 1 | 2.70E−06 | 6 | 1 | 1.00E−05 | 7.00E+01 |
| Ni | 0.1 | 1 | 1 | 1.00E+14 | 0 | 1 | 7.00E−06 | 6 | 1 | 1.00E−05 | 7.00E+01 |
| Ti | 0.1 | 1 | 1 | 1.00E+14 | 0 | 1 | 5.50E−05 | 6 | 1 | 1.00E−05 | 6.98E+01 |
| SS304 | 0.1 | 1 | 1 | 1.00E+14 | 0 | 1 | 7.20E−05 | 6 | 1 | 1.00E−05 | 6.97E+01 |
| Cu | 0.1 | 1 | 1 | 1.00E+14 | 0 | 1 | 1.70E−06 | 12 | 1 | 1.00E−05 | 1.30E+02 |
| Al | 0.1 | 1 | 1 | 1.00E+14 | 0 | 1 | 2.70E−06 | 12 | 1 | 1.00E−05 | 1.30E+02 |
| Ni | 0.1 | 1 | 1 | 1.00E+14 | 0 | 1 | 7.00E−06 | 12 | 1 | 1.00E−05 | 1.30E+02 |
| Ti | 0.1 | 1 | 1 | 1.00E+14 | 0 | 1 | 5.50E−05 | 12 | 1 | 1.01E−05 | 1.29E+02 |
| SS304 | 0.1 | 1 | 1 | 1.00E+14 | 0 | 1 | 7.20E−05 | 12 | 1 | 1.01E−05 | 1.29E+02 |
| Cu | 0.1 | 5 | 1 | 1.00E+14 | 0 | 1 | 1.70E−06 | 100 | 1 | 5.00E−05 | 2.10E+02 |
| Al | 0.1 | 5 | 1 | 1.00E+14 | 0 | 1 | 2.70E−06 | 100 | 1 | 5.00E−05 | 2.10E+02 |
| Ni | 0.1 | 5 | 1 | 1.00E+14 | 0 | 1 | 7.00E−06 | 100 | 1 | 5.01E−05 | 2.10E+02 |
| Ti | 0.1 | 5 | 1 | 1.00E+14 | 0 | 1 | 5.50E−05 | 100 | 1 | 5.06E−05 | 2.08E+02 |
| SS304 | 0.1 | 5 | 1 | 1.00E+14 | 0 | 1 | 7.20E−05 | 100 | 1 | 5.07E−05 | 2.07E+02 |

In what follows, a description of humic acid and graphene, the two main ingredients in the thin film coated on a metal foil, is presented.

Bulk natural flake graphite is a 3-D graphitic material with each particle being composed of multiple grains (a grain being a graphite single crystal or crystallite) with grain boundaries (amorphous or defect zones) demarcating neighboring graphite single crystals. Each grain is composed of multiple graphene planes that are oriented parallel to one another. A graphene plane in a graphite crystallite is composed of carbon atoms occupying a two-dimensional, hexagonal lattice. In a given grain or single crystal, the graphene planes are stacked and bonded via van der Waal forces in the crystallographic c-direction (perpendicular to the graphene plane or basal plane). Although all the graphene planes in one grain are parallel to one another, typically the graphene planes in one grain and the graphene planes in an adjacent grain are different in orientation. In other words, the orientations of the various grains in a graphite particle typically differ from one grain to another.

A graphite single crystal (crystallite) per se is anisotropic with a property measured along a direction in the basal plane (crystallographic a- or b-axis direction) being dramatically different than the property measured along the crystallographic c-axis direction (thickness direction). For instance, the thermal conductivity of a graphite single crystal can be up to approximately 1,920 W/mK (theoretical) or 1,800 W/mK (experimental) in the basal plane (crystallographic a- and b-axis directions), but that along the crystallographic c-axis direction is less than 10 W/mK (typically less than 5 W/mK). Further, the multiple grains or crystallites in a graphite particle are typically all oriented along different directions. Consequently, a natural graphite particle composed of multiple grains of different orientations exhibits an average property between these two extremes (i.e. typically <100 W/mK).

The constituent graphene planes (typically 30 nm-2 μm wide/long) of a graphite crystallite can be exfoliated and extracted or isolated from the graphite crystallite to obtain individual graphene sheets of carbon atoms provided the inter-planar van der Waals forces can be overcome. An isolated, individual graphene sheet of hexagonal carbon atoms is commonly referred to as single-layer graphene. A stack of multiple graphene planes bonded through van der Waals forces in the thickness direction with an inter-graphene plane spacing of 0.3354 nm is commonly referred to as a multi-layer graphene. A multi-layer graphene platelet has up to 300 layers of graphene planes (<100 nm in thickness), but more typically up to 30 graphene planes (<10 nm in thickness), even more typically up to 20 graphene planes (<7 nm in thickness), and most typically up to 10 graphene planes (commonly referred to as few-layer graphene in scientific community). Single-layer graphene and multi-layer graphene sheets are collectively called "nano graphene platelets" (NGPs). Graphene sheets/platelets or NGPs are a new class of carbon nano material (a 2-D nano carbon) that is distinct from the 0-D fullerene, the 1-D CNT, and the 3-D graphite.

Our research group pioneered the development of pristine graphene materials, isolated graphene oxide sheets, and related production processes as early as 2002: (1) B. Z. Jang and W. C. Huang, "Nano-scaled Graphene Plates," U.S. Pat. No. 7,071,258 (Jul. 4, 2006), application submitted on Oct. 21, 2002; (2) B. Z. Jang, et al. "Process for Producing Nano-scaled Graphene Plates," U.S. patent application Ser. No. 10/858,814 (Jun. 3, 2004) (U.S. Pat. Pub. No. 2005/0271574) (now abandoned); and (3) B. Z. Jang, A. Zhamu, and J. Guo, "Process for Producing Nano-scaled Platelets and Nanocomposites," U.S. patent application Ser. No. 11/509,424 (Aug. 25, 2006) (U.S. Pat. Pub. No. 2008/0048152) (now abandoned). Historically, Brodie first demonstrated the synthesis of graphite oxide in 1859 by adding a portion of potassium chlorate to a slurry of graphite in fuming nitric acid. In 1898, Staudenmaier improved on this procedure by using concentrated sulfuric acid as well as fuming nitric acid and adding the chlorate in multiple aliquots over the course of the reaction. This small change in the procedure made the production of highly oxidized graphite in a single reaction vessel significantly more practical. In 1958, Hummers reported the method most commonly used today: the graphite is oxidized by treatment with $KMnO_4$ and $NaNO_3$ in concentrated $H_2SO_4$. However, these earlier work failed to isolate and identify fully exfoliated and separated graphene oxide sheets. These studies also failed to disclose the isolation of pristine, non-oxidized single-layer or multiple-layer graphene sheets.

In real practice (e.g. as illustrated in FIG. 1(A)), NGPs are typically obtained by intercalating natural graphite particles 100 with a strong acid and/or oxidizing agent to obtain a graphite intercalation compound 102 (GIC) or graphite oxide (GO). The presence of chemical species or functional groups in the interstitial spaces between graphene planes serves to increase the inter-graphene spacing ($d_{002}$, as determined by X-ray diffraction), thereby significantly reducing the van der Waals forces that otherwise hold graphene planes together along the c-axis direction. The GIC or GO is most often produced by immersing natural graphite powder in a mixture of sulfuric acid, nitric acid (an oxidizing agent), and another oxidizing agent (e.g. potassium permanganate or sodium perchlorate). The resulting GIC (102) is actually some type of graphite oxide (GO) particles. This GIC or GO is then repeatedly washed and rinsed in water to remove excess acids, resulting in a graphite oxide suspension or dispersion, which contains discrete and visually discernible graphite oxide particles dispersed in water. There are two processing routes to follow after this rinsing step:

Route 1 involves removing water from the suspension to obtain "expandable graphite," which is essentially a mass of dried GIC or dried graphite oxide particles. Upon exposure of expandable graphite to a temperature in the range from typically 800-1,050° C. for approximately 30 seconds to 2 minutes, the GIC undergoes a rapid volume expansion by a factor of 30-300 to form "graphite worms" (104), which are each a collection of exfoliated, but largely un-separated graphite flakes that remain interconnected.

In Route 1A, these graphite worms (exfoliated graphite or "networks of interconnected/non-separated graphite flakes") can be re-compressed to obtain flexible graphite sheets or foils (106) that typically have a thickness in the range from 0.1 mm (100 μm)-0.5 mm (500 μm). Alternatively, one may choose to use a low-intensity air mill or shearing machine to simply break up the graphite worms for the purpose of producing the so-called "expanded graphite flakes" (108) which contain mostly graphite flakes or platelets thicker than 100 nm (hence, not a nano material by definition). These expanded graphite flakes may be made into a paper-like graphite mat (110).

Exfoliated graphite worms, expanded graphite flakes, and the recompressed mass of graphite worms (commonly referred to as flexible graphite sheet or flexible graphite foil) are all 3-D graphitic materials that are fundamentally different and patently distinct from either the 1-D nano carbon material (CNT or CNF) or the 2-D nano carbon material (graphene sheets or platelets, NGPs). Flexible graphite (FG) foils can be used as a heat spreader material, but exhibiting a maximum in-plane thermal conductivity of typically less than 500 W/mK (more typically <300 W/mK) and in-plane electrical conductivity no greater than 1,500 S/cm. These low conductivity values are a direct result of the many defects, wrinkled or folded graphite flakes, interruptions or gaps between graphite flakes, and non-parallel flakes (e.g. SEM image in FIG. 2). Many flakes are inclined with respect to one another at a very large angle (e.g. mis-orientation of 20-40 degrees).

In Route 1B, the exfoliated graphite is subjected to high-intensity mechanical shearing (e.g. using an ultrasonicator, high-shear mixer, high-intensity air jet mill, or high-energy ball mill) to form separated single-layer and multi-layer graphene sheets (collectively called NGPs, 112), as disclosed in our U.S. application Ser. No. 10/858,814. Single-layer graphene can be as thin as 0.34 nm, while multi-layer graphene can have a thickness up to 100 nm, but more typically less than 20 nm. Graphene sheets or platelets may then be made into a graphene paper or membrane (114).

Route 2 entails ultrasonicating the graphite oxide suspension for the purpose of separating/isolating individual graphene oxide sheets from graphite oxide particles. This is based on the notion that the inter-graphene plane separation has been increased from 0.3354 nm in natural graphite to 0.6-1.1 nm in highly oxidized graphite oxide, significantly weakening the van der Waals forces that hold neighboring planes together. Ultrasonic power can be sufficient to further separate graphene plane sheets to form separated, isolated, or discrete graphene oxide (GO) sheets. These graphene oxide sheets can then be chemically or thermally reduced to obtain "reduced graphene oxides" (RGO) typically having an oxygen content of 0.001%-10% by weight, more typically 0.01%-5% by weight, most typically and preferably less than 2% by weight.

For the purpose of defining the claims of the instant application, NGPs include discrete sheets/platelets of single-layer and multi-layer pristine graphene, graphene oxide, or reduced graphene oxide (RGO). Pristine graphene has essentially 0% oxygen. RGO typically has an oxygen content of 0.001%-5% by weight. Graphene oxide (including RGO) can have 0.001%-50% by weight of oxygen.

It may be noted that flexible graphite foils (obtained by compressing or roll-pressing exfoliated graphite worms) for electronic device thermal management applications (e.g. as a heat sink material) have the following major deficiencies: (1) As indicated earlier, flexible graphite (FG) foils exhibit a relatively low thermal conductivity, typically <500 W/mK and more typically <300 W/mK. By impregnating the exfoliated graphite with a resin, the resulting composite exhibits an even lower thermal conductivity (typically <<200 W/mK, more typically <100 W/mK). (2) Flexible graphite foils, without a resin impregnated therein or coated thereon, are of low strength, low rigidity, and poor structural integrity. The high tendency for flexible graphite foils to get torn apart makes them difficult to handle in the process of making a heat sink. As a matter of fact, the flexible graphite sheets (typically 50-200 μm thick) are so "flexible" that they are not sufficiently rigid to make a fin component material for a finned heat sink. (3) Another very subtle, largely ignored or overlooked, but critically important feature of FG foils is their high tendency to get flaky with graphite flakes easily coming off from FG sheet surfaces and emitting out to other parts of a microelectronic device. These highly electrically conducting flakes (typically 1-200 μm in lateral dimensions and >100 nm in thickness) can cause internal shorting and failure of electronic devices.

Similarly, solid NGPs (including discrete sheets/platelets of pristine graphene, GO, and RGO), when packed into a film, membrane, or paper sheet (114) of non-woven aggregates using a paper-making process, typically do not exhibit a high thermal conductivity unless these sheets/platelets are closely packed and the film/membrane/paper is ultra-thin (e.g. <1 μm, which is mechanically weak). This is reported in our earlier U.S. patent application Ser. No. 11/784,606 (Apr. 9, 2007) (U.S. Pat. Pub. No. 2008/0248275) (now U.S. Pat. No. 9,233,850). However, ultra-thin film or paper sheets (<10 μm) are difficult to produce in mass quantities, and difficult to handle when one tries to incorporate these thin films as a heat sink material. In general, a paper-like structure or mat made from platelets of graphene, GO, or RGO (e.g. those paper sheets prepared by vacuum-assisted filtration process) exhibit many defects, wrinkled or folded graphene sheets, interruptions or gaps between platelets, and non-parallel platelets (e.g. SEM image in FIG. 3(B)), leading to relatively poor thermal conductivity, low electric conductivity, and low structural strength. These papers or aggregates of discrete NGP, GO or RGO platelets alone (without a resin binder) also have a tendency to get flaky, emitting conductive particles into air.

Another prior art graphitic material is the pyrolytic graphite film, typically thinner than 100 μm. The process begins with carbonizing a polymer film (e.g. polyimide) at a carbonization temperature of 400-1,500° C. under a typical pressure of 10-15 kg/cm² for 10-36 hours to obtain a carbonized material, which is followed by a graphitization treatment at 2,500-3,200° C. under an ultrahigh pressure of 100-300 kg/cm² for 1-24 hours to form a graphitic film. It is technically utmost challenging to maintain such an ultrahigh pressure at such an ultrahigh temperature. This is a difficult, slow, tedious, energy-intensive, and extremely expensive process. Furthermore, it has been difficult to produce pyrolytic graphite film thinner than 10 μm or thicker than 100 μm from a polymer such as polyimide. This thickness-related problem is inherent to this class of materials due to their difficulty in forming into an ultra-thin (<10 μm) and thick film (>100 μm) while still maintaining an acceptable degree of polymer chain orientation and mechanical strength that are required of proper carbonization and graphitization.

A second type of pyrolytic graphite is produced by high temperature decomposition of hydrocarbon gases in vacuum followed by deposition of the carbon atoms to a substrate surface. This vapor phase condensation of cracked hydrocarbons is essentially a chemical vapor deposition (CVD) process. In particular, highly oriented pyrolytic graphite (HOPG) is the material produced by subjecting the CVD-deposited pyro-carbon to a uniaxial pressure at very high temperatures (typically 3,000-3,300° C.). This entails a thermo-mechanical treatment of combined and concurrent mechanical compression and ultra-high temperature for an extended period of time in a protective atmosphere; a very expensive, energy-intensive, time-consuming, and technically challenging process. The process requires ultra-high temperature equipment (with high vacuum, high pressure, or high compression provision) that is not only very expensive to make but also very expensive and difficult to maintain. Even with such extreme processing conditions, the resulting HOPG still possesses many defects, grain boundaries, and mis-orientations (neighboring graphene planes not parallel to each other), resulting in less-than-satisfactory in-plane properties. Typically, the best prepared HOPG sheet or block typically contains many poorly aligned grains or crystals and a vast amount of grain boundaries and defects.

Similarly, the most recently reported graphene thin film (<2 nm) prepared by catalytic CVD of hydrocarbon gas (e.g. $C_2H_4$) on Ni or Cu surface is not a single-grain crystal, but a poly-crystalline structure with many grain boundaries and defects. With Ni or Cu being the catalyst, carbon atoms obtained via decomposition of hydrocarbon gas molecules at 800-1,000° C. are deposited onto Ni or Cu foil surface to form a sheet of single-layer or few-layer graphene that is poly-crystalline. The grains are typically much smaller than 100 μm in size and, more typically, smaller than 10 μm in size. These graphene thin films, being optically transparent and electrically conducting, are intended for applications such as the touch screen (to replace indium-tin oxide or ITO glass) or semiconductor (to replace silicon, Si). Furthermore, the Ni- or Cu-catalyzed CVD process does not lend itself to the deposition of more than 5 graphene planes (typically <2 nm) beyond which the underlying Ni or Cu catalyst can no longer provide any catalytic effect. There has been no experimental evidence to indicate that CVD graphene layer thicker than 5 nm is possible. Both CVD graphene film and HOPG are extremely expensive.

The above discussion clearly indicates that every prior art method or process for producing graphene and graphitic thin film has major deficiencies. Hence, an urgent need exists to have a new class of carbon nano materials that are comparable or superior to graphene in terms of the properties essential to a current collector (e.g. electrical conductivity, thermal conductivity, contact resistance with the metal foil), strength, and compatibility with electrolyte of an intended battery or supercapacitor. One must also be able to produce these materials more cost-effectively, faster, more scalable, and in a more environmentally benign manner. The production process for such a new carbon nano material must require a reduced amount of undesirable chemical (or elimination of these chemicals all together), shortened process time, less energy consumption, reduced or eliminated effluents of undesirable chemical species into the drainage (e.g., sulfuric acid) or into the air (e.g., $SO_2$ and $NO_2$).

Humic acid (HA) is an organic matter commonly found in soil and can be extracted from the soil using a base (e.g. KOH). HA can also be extracted from a type of coal called leonardite, which is a highly oxidized version of lignite coal. HA extracted from leonardite contains a number of oxygenated groups (e.g. carboxyl groups) located around the edges of the graphene-like molecular center ($SP^2$ core of hexagonal carbon structure). This material is slightly similar to graphene oxide (GO) which is produced by strong acid oxidation of natural graphite. HA has a typical oxygen content of 5% to 42% by weight (other major elements being carbon, hydrogen, and nitrogen). An example of the molecular structure for humic acid, having a variety of components including quinone, phenol, catechol and sugar moieties, is given in Scheme 1 below (source: Stevenson F. J. "*Humus Chemistry: Genesis, Composition, Reactions*," John Wiley & Sons, New York 1994).

(Scheme 1)

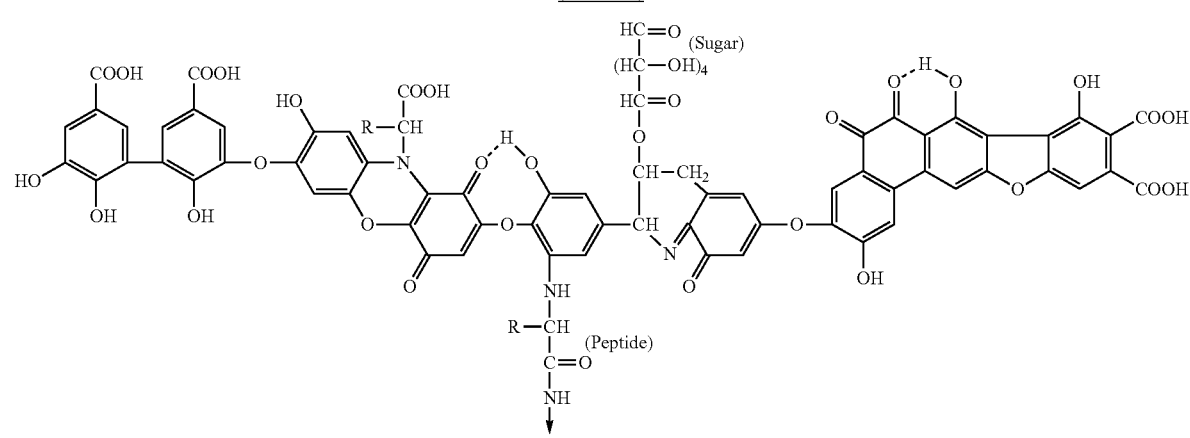

Non-aqueous solvents for humic acid include polyethylene glycol, ethylene glycol, propylene glycol, an alcohol, a sugar alcohol, a polyglycerol, a glycol ether, an amine based solvent, an amide based solvent, an alkylene carbonate, an organic acid, or an inorganic acid.

The present disclosure also provides a process for producing a highly oriented humic acid film (with or without externally added graphene sheets) and humic acid-derived graphitic film with a thickness from 2 nm to 30 µm (more typically and preferably from 5 nm to 10 µm, even more typically from 10 nm to 2 µm) and a physical density no less than 1.3 g/cm³ (up to 2.2 g/cm³). This film is chemically bonded to metal foil surfaces. In certain embodiments, the process comprises:

(a) preparing a dispersion of humic acid (HA) or chemically functionalized humic acid (CHA) having HA or CHA sheets dispersed in a liquid medium, wherein the HA sheets contain an oxygen content higher than 5% by weight or the CHA sheets contain non-carbon element content higher than 5% by weight; (In certain preferred embodiments, the HA or CHA dispersion further contains graphene sheets or molecules dispersed therein and the HA-to-graphene or CHA-to-graphene ratio is from 1/100 to 100/1. These graphene sheets may be selected from pristine graphene, graphene oxide, reduced graphene oxide, graphene fluoride, graphene bromide, graphene iodide, boron-doped graphene, nitrogen-doped graphene, chemically functionalized graphene, or a combination thereof.)

(b) dispensing and depositing the HA or CHA dispersion onto at least one primary surface of a metal foil (e.g. a Cu foil) to form a wet layer of HA or CHA, wherein the dispensing and depositing procedure includes subjecting the dispersion to an orientation-inducing stress; (This orientation-controlling stress, typically including a shear stress, enables the HA/CHA sheets (or sheet-like molecules) and graphene sheets (if present) to get aligned along planar directions of the metal foil substrate surface (e.g. Cu foil). Proper alignment of the HA/CHA and graphene sheets is essential to the chemical linking or merging between two or multiple HA/CHA sheets, or between HA/CHA sheets and graphene sheets during subsequent heat treatments.)

(c) partially or completely removing the liquid medium from the wet layer of HA or CHA to form a dried HA or CHA layer having hexagonal carbon planes and an inter-planar spacing $d_{002}$ of 0.4 nm to 1.3 nm as determined by X-ray diffraction; and (d) thermally treating the dried HA or CHA layer at a first heat treatment temperature higher than 80° C. for a sufficient period of time to produce the highly oriented humic acid film containing inter-connected or merged HA or CHA sheets that are substantially parallel to one another. This is schematically illustrated in FIG. 3(C). The humic acid film is also chemically bonded to the metal foil surface. These HA/CHA sheets typically also have been thermally reduced. This highly oriented humic acid film of reduced HA or CHA may be subjected to an additional step of compressing against the metal foil.

The process (with or without the step of compressing) can comprise an additional step (e) of further heat-treating the humic acid film of merged and reduced HA or CHA at a second heat treatment temperature higher than the first heat treatment temperature for a sufficient period of time to produce a graphitic film having an inter-planar spacing $d_{002}$ less than 0.4 nm and an oxygen content or non-carbon element content less than 5% by weight; and (f) compressing the graphitic film (e.g. against the Cu foil) to produce a highly conducting graphitic film bonded to the metal foil.

In an embodiment, step (e) includes heat-treating the highly oriented humic acid film at a second heat treatment temperature higher than the first heat treatment temperature (typically >300° C.) for a length of time sufficient for decreasing an inter-plane spacing $d_{002}$ to a value of from 0.3354 nm to 0.36 nm and decreasing the oxygen content or non-carbon content to less than 0.5% by weight. In a preferred embodiment, the second (or final) heat treatment temperature includes at least a temperature selected from (A) 100-300° C., (B) 300-1,500° C., (C) 1,500-2,500° C., and/or (D) 2,500-3,200° C. Preferably, the second heat treatment temperature includes a temperature in the range from 300-1,500° C. for at least 1 hour and then a temperature in the range from 1,500-3,200° C. for at least another hour.

Typically, if both the first and second heat treatment temperatures are below 1,500° C., the highly oriented humic acid (HOHA) film still contains planar molecules that are characteristic of humic acid molecules. The highly oriented humic acid (HOHA) film contains chemically bonded and merged hexagonal carbon planes, which are HA/CHA or combined HA/CHA-graphene planes. These planes (hexagonal structured carbon atoms having a small amount of oxygen-containing group) are parallel to one another.

This HOHA film, if exposed to a heat treatment temperature (HTT) of 1,500° C. or higher for a sufficient length of time, typically no longer contains any significant amount of humic acid molecules and essentially all HA/CHA sheets/molecules have been converted to graphene- or graphene oxide-like hexagonal carbon planes that are parallel to one another. The lateral dimensions (length or width) of these planes are huge, typically several times or even orders of magnitude larger than the maximum dimensions (length/width) of the starting HA/CHA sheets. The presently invented HOHA is essentially a "giant hexagonal carbon crystal" or "giant planar graphene-like layer" having all constituent graphene-like planes being essentially parallel to one another. This is a unique and new class of material that has not been previously discovered, developed, or suggested to possibly exist.

The oriented HA/CHA layer (HOHA film with no HTT>1,500° C.) is itself a very unique and novel class of material that surprisingly has great cohesion power (self-bonding, self-polymerizing, and self-crosslinking capability). These characteristics have not been previously taught or hinted in the prior art.

The above paragraphs have been written to describe a type of current collectors obtained by heat treating the HA- or HA/graphene mixture-bonded metal film as a two-layer or three-layer laminate. The HA or HA/graphene layer was not peeled off from the metal foil and heat-treated alone (without the metal foil). The resulting current collector does not contain a binder resin or adhesive. This type is herein referred to as Type-A current collector. This type of current collector can be heat-treated up to a maximum temperature close to the melting point of the underlying metal foil. However, certain metal foil (e.g. Cu, Ti, and steel) appears to be capable of catalyzing the chemical linking between HA sheets or between HA and graphene, enabling the formation of larger HA/graphene domains and fewer defects and leading to higher thermal and electrical conductivity and structural integrity that otherwise could not be achieved without invoking a much higher heat treatment temperature.

The preparation of Type-B current collector is described in the following two paragraphs:

Alternatively, the above procedures, from (a) to (d) or (e), can be conducted by depositing the dispersion of HA or HA/graphene mixture onto a plastic film or glass surface and, upon liquid removal, the resulting dried film is peeled off from the plastic film or glass so that the film can be subsequently heat treated at any desired temperature. The highly oriented HA film (after a heat treatment at a temperature from 80 to 1,500° C.) or the derived graphitic film (after a heat treatment at a temperature from 1,500 to 3,200° C.), as a free-standing film, is then bonded to one or both primary surfaces of a metal foil (e.g. Cu or Al foil) using a binder resin or adhesive. In comparison with Type-A current collector (wherein the highly oriented HA film or highly conducting graphitic film derived therefrom is prepared by directly depositing the thin film of HA or HA/graphene to a surface of a metal foil and chemically bonding to this surface without using a binder), such a Type-B current collector (obtained at a comparable final heat treatment temperature) has a lower in-plane thermal conductivity, lower in-plane electrical conductivity, higher contact resistance between layers, and less durable (easier to get delaminated) in a real liquid electrolyte environment inside a battery or supercapacitor.

In order to partially alleviating these issues, we chose to use binder materials that are more conducting than the typical binder resins (e.g. PVDF, SBR, etc. commonly used in lithium battery and supercapacitor industries). These include intrinsically conductive polymers (e.g. polyaniline, polypyrrole, polythiophene, etc.), pitch (e.g. isotropic pitch, meso-phase pitch, etc.), amorphous carbon (e.g. via chemical vapor infiltration), or a carbonized resin (heat-treating the current collector after the free-standing graphitic layer is bonded to the metal foil, converting resin binder to carbon binder in situ).

The following description is for both Type-A and Type-B current collectors.

Step (a) entails dispersing HA/CHA sheets or molecules in a liquid medium, which can be water or a mixture of water and an alcohol, for certain HA or CHA molecules that contain a significant amount of —OH and/or —COOH groups at the edges and/or on the planes of the HA/CHA sheets (e.g. having an oxygen content between 20% and 47% by weight, preferably between 30% and 47%).

When the volume fraction or weight fraction of HA/CHA exceeds a threshold value, the resulting dispersion is found to contain a liquid crystalline phase. Preferably, the HA/CHA suspension (dispersion) contains an initial volume fraction of HA/CHA sheets that exceeds a critical or threshold volume fraction for the formation of a liquid crystal phase prior to step (b). We have observed that such a critical volume fraction is typically equivalent to a HA/CHA weight fraction in the range from from 0.2% to 5.0% by weight of HA/CHA sheets in the dispersion. However, such a range of low HA/CHA contents is not particularly amenable to the formation of the desired thin films using a scalable process, such as casting and coating. The ability to produce thin films via casting or coating is highly advantageous and desirable since large-scaled and/or automated casting or coating systems are readily available, and the processes are known to be reliable for production of polymer thin films with consistently high quality. Therefore, we proceeded to conduct an in-depth and extensive study on the suitability for casting or coating from the dispersion containing a HA/CHA-based liquid crystalline phase. We discovered that by concentrating the dispersion to increase the HA/CHA contents from the range of 0.2% to 5.0% by weight to the range of 4% to 16% by weight of HA/CHA sheets, we obtain a dispersion that is highly suitable to large-scale production of thin graphene films. Most significantly and quite unexpectedly, the liquid crystalline phase is not only preserved, but often enhanced, making it more feasible for HA/CHA sheets to be oriented along preferred orientations during the casting or coating procedures. In particular, the HA/CHA sheets in a liquid crystal state containing 4% to 16% by weight of HA/CHA sheets have the highest tendency to get readily oriented under the influence of a shear stress created by a commonly used casting or coating process.

Thus, in step (b), the HA/CHA suspension is formed into a thin-film layer preferably under the influence of a shear stress that promotes a laminar flow. One example of such a shearing procedure is casting or coating a thin film of HA/CHA suspension using a slot-die coating machine. This procedure is similar to a layer of polymer solution being coated onto a solid substrate. The roller, "doctor's blade", or wiper creates a shear stress when the film is shaped, or when there is a relative motion between the roller/blade/wiper and the supporting substrate at a sufficiently high relative motion speed. Quite unexpectedly and significantly, such a shearing action enables the planar HA/CHA sheets to well align along, for instance, a shearing direction. Further surprisingly, such a molecular alignment state or preferred orientation is not disrupted when the liquid components in the HA/CHA suspension are subsequently removed to form a well-packed layer of highly aligned HA/CHA sheets that are at least partially dried. The dried layer has a high birefringence coefficient between an in-plane direction and the normal-to-plane direction.

The present disclosure includes the discovery of a facile amphiphilic self-assembly approach to fabricate HA/CHA-based thin films with desired hexagonal plane orientation. HA containing 5-46% by weight of oxygen may be considered a negatively charged amphiphilic molecule due to its combination of hydrophilic oxygen-containing functional groups and a hydrophobic basal plane. For a CHA, the functional groups can be made to be hydrophilic or hydrophobic. The successful preparation of the HA/CHA films with unique hexagonal, graphene-like plane orientations does not require complex procedures. Rather, it is achieved by tailoring HA/CHA synthesis and manipulating the liquid crystalline phase formation and deformation behaviors to enable the self-assembly of HA/CHA sheets in a liquid crystalline phase.

The HA/CHA suspension was characterized using atomic force microscopy (AFM), Raman spectroscopy, and FTIR to confirm its chemical state. Finally, the presence of lyotropic meso-morphism of HA sheets (liquid crystalline HA phase) in aqueous solution was demonstrated through cross-polarized light observation.

Two major aspects are considered to determine if a 1-D or 2-D species can form a liquid crystalline phase in a liquid medium: the aspect ratio (the length/width/diameter-to-thickness ratio) and sufficient dispersibility or solubility of this material in the liquid medium. HA or CHA sheets feature high anisotropy, with monatomic or few-atom thickness (t) and normally micrometer-scale lateral width (w). According to Onsager's theory, high aspect ratio 2D sheets can form liquid crystals in dispersions, when their volume fraction exceeds a critical value:

$$V_c \approx 4t/w \qquad \text{(Eq. 1)}$$

Given the thickness of a graphene-like plane being 0.34 nm and a width of 1 μm, the required critical volume would be $V_c \approx 4t/w = 4 \times 0.34/1,000 = 1.36 \times 10^{-3} = 0.136\%$. However, pristine graphene sheets are not soluble in water and poorly dispersible in common organic solvents (maximum volume fraction, $V_m$, ~$0.7 \times 10^{-5}$ in N-methylpyrrolidone (NMP) and ~$1.5 \times 10^{-5}$ in ortho-dichlorobenzene), owing to their strong π-π stacking attraction. Fortunately, the molecular structure of HA or CHA can be made to exhibit good dispersibility in water and polar organic solvents, such as alcohol, N,N-dimethyl formamide (DMF) and NMP, due to the numerous oxygen-containing functional groups attached to its edges. Naturally occurring HA (e.g. that from coal) is also highly soluble in non-aqueous solvents for humic acid include polyethylene glycol, ethylene glycol, propylene glycol, an alcohol, a sugar alcohol, a polyglycerol, a glycol ether, an amine based solvent, an amide based solvent, an alkylene carbonate, an organic acid, an inorganic acid, or a mixture thereof.

Although, presumably the critical volume fraction of HA/CHA can be lower than 0.2% or critical weight fraction lower than 0.3% according to theoretical prediction, we have observed that the critical weight fractions for HA/CHA sheets to form liquid crystals are significantly higher than 0.4% by weight. The most stable liquid crystals are present when the weight fraction of HA/CHA sheets is in the range from 0.6%-5.0%, which enable high stability over a wide temperature range. To study the effect of HA/CHA size on the formation of its liquid crystalline structure, HA/CHA samples were prepared using a pH-assisted selective sedimentation technique. The lateral sizes of HA/CHA sheets were assessed by dynamic light scattering (DLS) via three different measurement modes, as well as AFM.

During the investigation of HA/CHA liquid crystals we made an unexpected but highly significant discovery: The liquid crystalline phase of HA/CHA sheets in water and other solvents can be easily disrupted or destroyed with mechanical disturbances (e.g. mechanical mixing, shearing, turbulence flow, etc.). The mechanical stability of these liquid crystals can be significantly improved if the concentration of HA/CHA sheets is gradually increased to above 5% (preferably from 5% to 16% by weight) by carefully removing (e.g. vaporizing) the liquid medium without mechanically disturbing the liquid crystalline structure. We further observed that with a HA/CHA weight fraction in this range of 5-16%, HA/CHA sheets are particularly amenable to forming desired orientations during casting or coating to form thin films.

Thermodynamically, the process of amphiphilic HA/CHA self-assembly into a liquid crystalline phase is an interplay of the enthalpy change ($\Delta H$) and entropy change ($\Delta S$) as shown in Eq. (2):

$$\Delta G_{self-assembly} = \Delta H_{self-assembly} - T\Delta S_{self-assembly} \quad (2)$$

Previous studies into the thermodynamic driving force for amphiphilic self-assembly into liquid crystal phases indicate that the entropic contribution plays a dominant role, while the enthalpy change is unfavorable in most cases. Onsager's theory predicts that high aspect ratio particles can form liquid crystal phases above a critical volume fraction due to a net gain in entropy as the loss of orientational entropy is compensated for by an increased translational entropy. Specifically, higher aspect ratio particles favor the formation of long-range liquid crystalline phases. Another possible reason for the HA/CHA aspect ratio effect could be the structural corrugation of HA/CHA sheets in solvent as the restoring force originated from bending the sheets is much weaker than that along the sheet. It was found that the degree of HA/CHA corrugated morphology in solvent could be further enhanced if its aspect ratio is increased. This corrugated configuration will significantly affect both the intra and intermolecular interactions of HA/CHA in suspension.

To achieve long-range ordering in an aqueous dispersion, well-exfoliated HA/CHA sheets with strong long-range electrostatic repulsion are required. Formation of liquid crystal structures out of colloidal particles typically requires a delicate balance of long-range repulsive forces, such as electrostatic forces, and short-range attractive forces, such as van der Waals forces and π-π interactions. If the long-range repulsive forces are not strong enough to overcome the short-range attractive forces, aggregation of colloidal particles or only weak formation of a lyotropic liquid crystal with small periodicity will inevitably occur. In the HA/CHA aqueous dispersion, long-range repulsive interactions are offered by the electrical double layers formed by the ionized oxygen functional groups. Although HA/CHA sheets still contain a considerable portion of hydrophobic domains, attractive π-π interactions and van der Waals forces can be effectively overcome by adjusting the long-range electrostatic repulsive forces The chemical composition of HA/CHA plays an important role in tailoring the electrostatic interaction in an aqueous or organic solvent dispersion. The increase of surface charge density will lead to an increase in the strength of the electrostatic repulsion against the attractive forces. The ratio of the aromatic and oxygenated domains can be easily tuned by the level of hexagonal carbon plane oxidation or chemical modification. The Fourier transform infrared spectroscopy under attenuated total reflectance mode (FTIR-ATR) results of the HA/CHA indicate that oxidized species (hydroxyl, epoxy, and carboxyl groups) exist on the HA/CHA surfaces. Thermogravimetric analysis (TGA) in nitrogen was used to probe the oxygen functional group density on the HA/CHA surface. For a highly oxidized HA, a mass loss of ~28% by weight is found at around 250° C. and is attributed to the decomposition of labile oxygen-containing species. Below 160° C., a mass loss of ~16 wt % is observed, corresponding to desorption of physically absorbed water. The X-ray photoelectron spectroscopy (XPS) result of HA shows that an atomic ratio of C/O is about 1.9. This suggests that the HA has a relatively high density of oxygen functional groups. In addition, we also prepared HA containing a lower density of oxygen functional groups by simply varying the thermal or chemical reduction time and temperature of heavily oxidized HA (e.g. from leonardite coal). We have observed that liquid crystals can be found with oxygen weight fractions preferentially in the range from 5%-40%, more preferably 5%-30%, and most preferably 5%-20%.

The colloidal interaction between HA sheets can be significantly influenced by the ionic strength, because the Debye screening length ($\kappa^{-1}$) can be effectively increased by reducing the concentration of free ions surrounding HA sheets. The electrostatic repulsion of the HA liquid crystal in water could decrease as the salt concentration increases. As a result, more water is expelled from the HA interlamellar space with an accompanying reduction in d spacing. Thus, ionic impurities in the HA dispersions should be sufficiently removed, as it is a crucial factor influencing the formation of HA liquid crystal structure.

However, we have also found that introduction of some small amount of polymer (up to 10% by weight, but preferably up to 5% by weight, and most preferably up to only 2%) can help stabilize the liquid crystal phase when the HA/CHA dispersion is subjected to casting or coating operations. With proper functional groups and concentrations, the GO/CFG orientation in the resultant film could be enhanced. This also has never been taught or hinted in previous open or patent literature.

The dried HA/CHA layer may then be subjected to heat treatments. A properly programmed heat treatment procedure can involve at least two heat treatment temperatures (first temperature for a period of time and then raised to a second temperature and maintained at this second temperature for another period of time), or any other combination of at least two heat treatment temperatures (HTT) that involve an initial treatment temperature (first temperature) and a final HTT, higher than the first.

The first heat treatment temperature is for chemical linking and thermal reduction of HA/CHA and is conducted at the first temperature of >80° C. (can be up to 1,000° C., but preferably up to 700° C., and most preferably up to 300° C.). This is herein referred to as Regime 1:

Regime 1 (up to 300° C.): In this temperature range (the initial chemical linking and thermal reduction regime), chemical combination, polymerization (edge-to-edge merging), and cross-linking between adjacent HA/CHA sheets begin to occur. Multiple HA/CHA sheets are packed and chemically bonded together side by side and edge to edge to form an integrated layer of graphene oxide-like entity. In addition, a HA/CHA layer primarily undergoes thermally-induced reduction reactions, leading to a reduction of oxygen content to approximately 5% or lower. This treatment results in a reduction of inter-graphene spacing from approximately 0.8-1.2 nm (as dried) down to approximately 0.4 nm, and an increase in in-plane thermal conductivity from approximately 100 W/mK to 500 W/mK. Even with such a low temperature range, some chemical linking between HA/CHA sheets occurs. The HA/CHA sheets remain well-aligned, but the inter-graphene plane spacing remains relatively large (0.4 nm or larger). Many O-containing functional groups survive.

The highest or final HTT that the GO mass experiences may be divided into three distinct HTT regimes:

Regime 2 (300° C.-1,500° C.): In this mainly chemical linking regime, additional thermal reduction and extensive chemical combination, polymerization, and cross-linking between adjacent HA/CHA sheets occur. The chemical linking between HA/CHA and graphene sheets (e.g. GO sheets), if present, also occurs. The oxygen content is reduced to typically below 1% after chemical linking, resulting in a reduction of inter-graphene spacing to approximately 0.35 nm. This implies that some initial graphitization has already begun at such a low temperature, in stark contrast to conventional graphitizable materials (such as carbonized polyimide film) that typically require a temperature as high as 2,500° C. to initiate graphitization. This is another distinct feature of the presently invented HOHA film and its production processes. These chemical linking reactions result in an increase in in-plane thermal conductivity to 850-1,250 W/mK, and/or in-plane electrical conductivity to 3,500-4,500 S/cm.

Regime 3 (1,500-2,500° C.): In this ordering and re-graphitization regime, extensive graphitization or graphene plane merging occurs, leading to significantly improved degree of structural ordering. As a result, the oxygen content is reduced to typically 0.01% and the inter-graphene spacing to approximately 0.337 nm (achieving degree of graphitization from 1% to approximately 80%, depending upon the actual HTT and length of time). The improved degree of ordering is also reflected by an increase in in-plane thermal conductivity to >1,300-1,500 W/mK, and/or in-plane electrical conductivity to 5,000-7,000 S/cm.

Regime 4 (higher than 2,500° C.): In this re-crystallization and perfection regime, extensive movement and elimination of grain boundaries and other defects occur, resulting in the formation of nearly perfect single crystals or poly-crystalline graphene crystals with huge grains, which can be orders of magnitude larger than the original grain sizes of the starting HA/CHA sheets. The oxygen content is essentially eliminated, typically 0.01%-0.1%. The inter-graphene spacing is reduced to down to approximately 0.3354 nm (degree of graphitization from 80% to nearly 100%), corresponding to that of a perfect graphite single crystal. Quite interestingly, the graphene poly-crystal has all the graphene planes being closely packed and bonded, and all the planes are aligned along one direction, a perfect orientation. Such a perfectly oriented structure has not been produced even with the HOPG that was produced by subjecting pyrolytic graphite concurrently to an ultra-high temperature (3,400° C.) under an ultra-high pressure (300 kg/cm$^2$). The highly oriented graphene structure can achieve such a highest degree of perfection with a significantly lower temperature and an ambient (or slightly higher compression) pressure. The structure thus obtained exhibits an in-plane thermal conductivity from 1,500 up to slightly >1,700 W/mK, and in-plane electrical conductivity to a range from 15,000 to 20,000 S/cm.

The presently invented highly oriented HA-derived structure can be obtained by heat-treating the HA/CHA layer with a temperature program that covers at least the first regime (typically requiring 1-24 hours in this temperature range), more commonly covers the first two regimes (1-10 hours preferred), still more commonly the first three regimes (preferably 0.5-5 hours in Regime 3), and most commonly all the 4 regimes (Regime 4, for 0.5 to 2 hour, may be implemented to achieve the highest conductivity).

X-ray diffraction patterns were obtained with an X-ray diffractometer equipped with CuKcv radiation. The shift and broadening of diffraction peaks were calibrated using a silicon powder standard. The degree of graphitization, g, was calculated from the X-ray pattern using the Mering's Eq, $d_{002}=0.3354$ g$+0.344$ (1−g), where $d_{002}$ is the interlayer spacing of graphite or graphene crystal in nm. This equation is valid only when $d_{002}$ is equal or less than approximately 0.3440 nm. The HOHA having a $d_{002}$ higher than 0.3440 nm reflects the presence of oxygen-containing functional groups (such as —OH, >0, and —COOH on graphene-like plane surfaces) that act as a spacer to increase the inter-graphene spacing.

Another structural index that can be used to characterize the degree of ordering of the presently invented HOHA-derived graphitic film and conventional graphite crystals is the "mosaic spread," which is expressed by the full width at half maximum of a rocking curve (X-ray diffraction intensity) of the (002) or (004) reflection. This degree of ordering characterizes the graphite or graphene crystal size (or grain size), amounts of grain boundaries and other defects, and the degree of preferred grain orientation. A nearly perfect single crystal of graphite is characterized by having a mosaic spread value of 0.2-0.4. Most of our HOHA-derived graphitic samples have a mosaic spread value in this range of 0.2-0.4 (if produced with a heat treatment temperature (HTT) no less than 2,500° C.). However, some values are in the range from 0.4-0.7 if the HTT is between 1,500 and 2,500° C., and in the range from 0.7-1.0 if the HTT is between 300 and 1,500° C.

HA or graphene may be functionalized through various chemical routes. In one preferred embodiment, the resulting functionalized HA or functionalized graphene (collectively denoted as Gn) may broadly have the following formula(e):

[Gn]—R$_m$ wherein m is the number of different functional group types (typically between 1 and 5), R is selected from SO$_3$H, COOH, NH$_2$, OH, R'CHOH, CHO, CN, COCl, halide, COSH, SH, COOR', SR', SiR'$_3$, Si(—OR'—)$_y$R'$_{3-y}$, Si(—O—SiR'$_2$—)OR', R", Li, AlR'$_2$, Hg—X, TlZ$_2$ and Mg—X; wherein y is an integer equal to or less than 3, R' is hydrogen, alkyl, aryl, cycloalkyl, or aralkyl, cycloaryl, or poly(alkyle-ther), R" is fluoroalkyl, fluoroaryl, fluorocycloalkyl, fluoro-aralkyl or cycloaryl, X is halide, and Z is carboxylate or trifluoroacetate.

Assuming that a polymer, such as epoxy resin, and HA or graphene sheets can be combined to make a coating composition, then the function group —NH$_2$ is of particular interest. For example, a commonly used curing agent for epoxy resin is diethylenetriamine (DETA), which can have 2 or more —NH$_2$ groups. One of the —NH$_2$ groups may be bonded to the edge or surface of a graphene sheet and the remaining un-reacted —NH$_2$ groups will be available for reacting with epoxy resin later. Such an arrangement provides a good interfacial bonding between the HA (or graphene) sheet and the resin additive.

Other useful chemical functional groups or reactive molecules may be selected from the group consisting of amidoamines, polyamides, aliphatic amines, modified aliphatic amines, cycloaliphatic amines, aromatic amines, anhydrides, ketimines, diethylenetriamine (DETA), triethylene-tetramine (TETA), tetraethylene-pentamine (TEPA), polyethylene polyamine, polyamine epoxy adduct, phenolic hardener, non-brominated curing agent, non-amine curatives, and combinations thereof. These functional groups are multi-functional, with the capability of reacting with at least two chemical species from at least two ends. Most importantly, they are capable of bonding to the edge or surface of graphene or HA using one of their ends and, during subsequent curing stage, are able to react with a resin at one or two other ends.

The above-described [Gn]—R$_m$ may be further functionalized. The resulting CFGs include compositions of the formula:

[Gn]-A$_m$, where A is selected from OY, NHY, O=C—OY, P=C—NR'Y, O=C—SY, O=C—Y, —CR'1-OY, N'Y or C'Y, and Y is an appropriate functional group of a protein, a peptide, an amino acid, an enzyme, an antibody, a nucleotide, an oligonucleotide, an antigen, or an enzyme substrate, enzyme inhibitor or the transition state analog of an enzyme substrate or is selected from R'—OH, R'—NR'$_2$, R'SH, R'CHO, R'CN, R'X, R'N+(R')$_3$X$^-$, R'SiR'$_3$, R'Si(—OR'—)$_y$R'$_{3-y}$, R'Si(—O—SiR'$_2$—)OR', R'—R", R'—N—CO, (C$_2$H$_4$-O—)$_w$H, (—C$_3$H$_6$O—)$_w$H, (—C$_2$H$_4$O)$_w$—R', (C$_3$H$_6$O)$_w$—R', R', and w is an integer greater than one and less than 200.

The HA and/or graphene sheets may also be functionalized to produce compositions having the formula:

[Gn]—[R'-A]$_m$ where m, R' and A are as defined above. The compositions of the disclosure also include CHAs upon which certain cyclic compounds are adsorbed. These include compositions of matter of the formula:

[Gn]—[X—R$_a$]$_m$ where a is zero or a number less than 10, X is a polynuclear aromatic, polyheteronuclear aromatic or metallopolyheteronuclear aromatic moiety and R is as defined above. Preferred cyclic compounds are planar. More preferred cyclic compounds for adsorption are porphyrins and phthalocyanines. The adsorbed cyclic compounds may be functionalized. Such compositions include compounds of the formula:

[Gn]—[X-A$_a$]$_m$ where m, a, X and A are as defined above.

The functionalized HA or graphene of the instant disclosure can be directly prepared by sulfonation, electrophilic addition to deoxygenated GO surfaces, or metallation. The graphene or HA sheets can be processed prior to being contacted with a functionalizing agent. Such processing may include dispersing the graphene or HA sheets in a solvent. In some instances the sheets may then be filtered and dried prior to contact. One particularly useful type of functional groups is the carboxylic acid moieties, which naturally exist on the surfaces of HAs if they are prepared from acid intercalation route discussed earlier. If an additional amount of carboxylic acid is needed, the HA sheets may be subjected to chlorate, nitric acid, or ammonium persulfate oxidation.

Carboxylic acid functionalized graphene sheets are particularly useful because they can serve as the starting point for preparing other types of functionalized graphene or HA sheets. For example, alcohols or amides can be easily linked to the acid to give stable esters or amides. If the alcohol or amine is part of a di- or poly-functional molecule, then linkage through the O— or NH— leaves the other functionalities as pendant groups. These reactions can be carried out using any of the methods developed for esterifying or aminating carboxylic acids with alcohols or amines as known in the art. Examples of these methods can be found in G. W. Anderson, et al., J. Amer. Chem. Soc. 86, 1839 (1964), which is hereby incorporated by reference in its entirety. Amino groups can be introduced directly onto graphitic fibrils by treating the fibrils with nitric acid and sulfuric acid to obtain nitrated fibrils, then chemically reducing the nitrated form with a reducing agent, such as sodium dithionite, to obtain amino-functionalized fibrils.

We have found that the aforementioned functional groups can be attached to HA or graphene sheet surfaces or edges for one or several of the following purposes: (a) for improved dispersion of graphene or HA in a desired liquid medium; (b) enhanced solubility of graphene or HA in a liquid medium so that a sufficient amount of graphene or HA sheets can be dispersed in this liquid that exceed the critical volume fraction for liquid crystalline phase formation; (c) enhanced film-forming capability so that thin film of otherwise discrete sheets of graphene or HA can be coated or cast; (d) improved capability of graphene or HA sheets to get oriented due to modifications to the flow behaviors; and (e) enhanced capability for graphene or HA sheets to get chemically linked and merged into larger or wider graphene planes.

The present disclosure also provides a rechargeable battery that contains a presently invented graphene oxide thin film-bonded metal foil as an anode current collector and/or a cathode current collector. This can be any rechargeable battery, such as a zinc-air cell, a nickel metal hydride cell, a sodium-ion cell, a sodium metal cell, a magnesium-ion cell, or a magnesium metal cell, just to name a few. This invented battery can be a rechargeable lithium battery containing the unitary graphene layer as an anode current collector or a cathode current collector, which lithium battery can be a lithium-sulfur cell, a lithium-selenium cell, a lithium sulfur/ selenium cell, a lithium-ion cell, a lithium-air cell, a lithium-graphene cell, or a lithium-carbon cell. Another embodiment of the disclosure is a capacitor containing the current collector of the present disclosure as an anode current collector or a cathode current collector, which capacitor is a symmetric ultracapacitor, an asymmetric ultracapacitor cell, a hybrid supercapacitor-battery cell, or a lithium-ion capacitor cell As an example, the present disclosure provides a rechargeable lithium-metal cell composed of a current collector at the anode, a lithium film or foil as the anode, a porous separator/electrolyte layer, a cathode containing a cathode active material (e.g. lithium-free $V_2O_5$ and $MnO_2$), and a current collector. Either or both the anode current collector and cathode current collector can be a HA-based current collector of the present disclosure (i.e. derived from highly oriented thin film of HA or a HA/graphene mixture).

Another example of the present disclosure is a lithium-ion capacitor (or hybrid supercapacitor) composed of a current collector at the anode, a graphite or lithium titanate anode, a porous separator soaked with liquid or gel electrolyte, a cathode containing a cathode active material (e.g. activated carbon having a high specific surface area), and a current collector. Again, either or both the anode current collector and cathode current collector can be a HA-based current collector of the present disclosure.

Yet another example of the present disclosure is another lithium-ion capacitor or hybrid supercapacitor, which is composed of a current collector at the anode, a graphite anode (and a sheet of lithium foil as part of the anode), a porous separator soaked with liquid electrolyte, a cathode containing a cathode active material (e.g. activated carbon having a high specific surface area), and a current collector. Again, either or both the anode current collector and cathode current collector can be a HA-based current collector of the present disclosure.

Still another example of the present disclosure is a lithium-graphene cell composed of a current collector at the anode, a porous, nano-structured anode (e.g. comprising graphene sheets having high surface areas upon which returning lithium ions can deposit during cell recharge, which are mixed with surface-stabilized lithium powder particles, or having a sheet of lithium foil attached to the nano-structure), a porous separator soaked with liquid electrolyte, a cathode containing a graphene-based cathode active material (e.g. graphene, graphene oxide, or graphene fluoride sheets having high specific surface areas to capture lithium ions during cell discharge), and a cathode current collector. Again, either or both the anode current collector and cathode current collector can be a HA-based current collector of the present disclosure.

Example 1: Humic Acid and Reduced Humic Acid from Leonardite

Humic acid can be extracted from leonardite by dispersing leonardite in a basic aqueous solution (pH of 10) with a very high yield (in the range from 75%). Subsequent acidification of the solution leads to precipitation of humic acid powder. In an experiment, 3 g of leonardite was dissolved by 300 ml of double deionized water containing IM KOH (or $NH_4OH$) solution under magnetic stirring. The pH value was adjusted to 10. The solution was then filtered to remove any big particles or any residual impurities.

The resulting humic acid dispersion, containing HA alone or HA with the presence of graphene oxide sheets (GO prepared in Example 3 described below), was coated onto a Cu foil or Ti foil surface form a series of HA-bonded Cu foil or Ti foil films for subsequent heat treatments to obtain Type-A current collectors.

For comparison, similar films were cast onto glass surface and then peeled off prior to subsequent heat treatments for the preparation of Type-B current collectors.

Example 2: Preparation of Humic Acid from Coal and HA-Bonded Metal Foil Current Collectors In a typical procedure, 300 mg of coal was suspended in concentrated sulfuric acid (60 ml) and nitric acid (20 ml), and followed by cup sonication for 2 h. The reaction was then stirred and heated in an oil bath at 100 or 120° C. for 24 h. The solution was cooled to room temperature and poured into a beaker containing 100 ml ice, followed by a step of adding NaOH (3M) until the pH value reached 7.

In one experiment, the neutral mixture was then filtered through a 0.45-mm polytetrafluoroethylene membrane and the filtrate was dialyzed in 1,000 Da dialysis bag for 5 days. For the larger humic acid sheets, the time can be shortened to 1 to 2 h using cross-flow ultrafiltration. After purification, the solution was concentrated using rotary evaporation to obtain solid humic acid sheets. These humic sheets alone and their mixtures with graphene sheets were re-dispersed in a solvent (ethylene glycol and alcohol, separately) to obtain several dispersion samples for subsequent casting or coating onto Al foil and stainless steel foils. Both Type-A and Type B current collectors were prepared.

Example 3: Preparation of Graphene Oxide (GO) Sheets from Natural Graphite Powder Natural graphite from Ashbury Carbons was used as the starting material. GO was obtained by following the well-known modified Hummers method, which involved two oxidation stages. In a typical procedure, the first oxidation was achieved in the following conditions: 1100 mg of graphite was placed in a 1000 mL boiling flask. Then, 20 g of $K_2S_2O_8$, 20 g of $P_2O_5$, and 400 mL of a concentrated aqueous solution of $H_2SO_4$ (96%) were added in the flask. The mixture was heated under reflux for 6 hours and then let without disturbing for 20 hours at room temperature. Oxidized graphite was filtered and rinsed with abundant distilled water until a pH value >4.0 was reached. A wet cake-like material was recovered at the end of this first oxidation.

For the second oxidation process, the previously collected wet cake was placed in a boiling flask that contains 69 mL of a concentrated aqueous solution of $H_2SO_4$ (96%). The flask was kept in an ice bath as 9 g of $KMnO_4$ was slowly added. Care was taken to avoid overheating. The resulting mixture was stirred at 35° C. for 2 hours (the sample color turning dark green), followed by the addition of 140 mL of water. After 15 min, the reaction was halted by adding 420 mL of water and 15 mL of an aqueous solution of 30 wt % $H_2O_2$. The color of the sample at this stage turned bright yellow. To remove the metallic ions, the mixture was filtered and rinsed with a 1:10 HCl aqueous solution. The collected material was gently centrifuged at 2700 g and rinsed with deionized water. The final product was a wet cake that contained 1.4 wt % of GO, as estimated from dry extracts. Subsequently, liquid dispersions of GO platelets were obtained by lightly sonicating wet-cake materials, which were diluted in deionized water.

On a separate basis, water suspensions containing mixtures of GO and humic acid at various GO proportions (1%, 10%, 20%, 30%, 40%, 50%, 60%, 70%, 80%, 90%, and 99%) were prepared and slot-die coated to produce thin films of various compositions.

Example 4: Preparation of Oriented Films Containing a Mixture of Humic Acid and Pristine Graphene Sheets (0% Oxygen)

In a typical procedure, five grams of graphite flakes, ground to approximately 20 μm or less in sizes, were dispersed in 1,000 mL of deionized water (containing 0.1% by weight of a dispersing agent, Zonyl® FSO from DuPont) to obtain a suspension. An ultrasonic energy level of 85 W (Branson S450 Ultrasonicator) was used for exfoliation, separation, and size reduction of graphene sheets for a period of 15 minutes to 2 hours. The resulting graphene sheets are pristine graphene that have never been oxidized and are oxygen-free and relatively defect-free. Pristine graphene is essentially free from any non-carbon elements.

The suspension after ultrasonication contains pristine graphene sheets dispersed in water and a surfactant dissolved therein. Humic acid was then added into the suspension and the resulting mixture suspension was further ultrasonicated for 10 minutes to facilitate uniform dispersion and mixing. The dispersion was then coated onto Cu and Ti foil and, for comparison, onto glass and PET films, prior to heat treatments.

Example 5: Preparation of Highly Oriented Graphitic Films from Mixtures of Graphene Fluoride Sheets and Humic Acid Several processes have been used by us to produce GF, but only one process is herein described as an example. In a typical procedure, highly exfoliated graphite (HEG) was prepared from intercalated compound $C_2F \cdot xClF_3$. HEG was further fluorinated by vapors of chlorine trifluoride to yield fluorinated highly exfoliated graphite (FHEG). Pre-cooled Teflon reactor was filled with 20-30 mL of liquid pre-cooled $ClF_3$, the reactor was closed and cooled to liquid nitrogen temperature. Then, no more than 1 g of HEG was put in a container with holes for $ClF_3$ gas to access and situated inside the reactor. In 7 days a gray-beige product with approximate formula $C_2F$ was formed.

Subsequently, a small amount of FHEG (approximately 0.5 mg) was mixed with 20-30 mL of an organic solvent (methanol and ethanol, separately) and subjected to an ultrasound treatment (280 W) for 30 min, leading to the formation of homogeneous yellowish dispersions. Humic acid was then added to these dispersions at various HA-to-GF ratios. The dispersions were then made into thin films supported by Cu foil using comma coating. The highly oriented HA films were then heat-treated to various extents to obtain highly conducting graphitic films.

Example 6: Preparation of the HOHA Films Containing Nitrogenated Graphene Sheets and Humic Acid Graphene oxide (GO), synthesized in Example 3, was finely ground with different proportions of urea and the pelletized mixture heated in a microwave reactor (900 W) for 30 s. The product was washed several times with deionized water and vacuum dried. In this method graphene oxide gets simultaneously reduced and doped with nitrogen. The products wre obtained with graphene/urea mass ratios of 1:0.5, 1:1 and 1:2. and the nitrogen contents of these samples were 14.7, 18.2 and 17.5 wt. % respectively as determined by elemental analysis. These nitrogenataed graphene sheets remain dispersible in water. Various amounts of HA, having oxygen contents of 20.5% to 45%, were added into the suspensions.

The resulting suspension of nitrogenated graphene-HA dispersions were then coated onto a plastic film substrate to form wet films, which were then dried and peeled off from the plastic film and subjected to heat treatments at various heat treatment temperatures, from 80 to 2,900° C. to obtain highly oriented humic acid (HOHA) films (if final HTT<1,500° C.) or highly ordered and conducting graphitic films (if 1,500° C. or higher). These films were then bonded to Ti and Cu surfaces, using a resin binder, to make Type-B current collectors. Additionally, for comparison purposes, some amounts of suspension of nitrogenated graphene-HA dispersions were also coated onto Ti and Cu foil surfaces to form wet films, which were then dried and heat-treated up to 1,500° C. and 1,250° C., respectively.

Example 7: Preparation of Nematic Liquid Crystals from Humic Acid Sheets and Highly Conducting Films Produced Therefrom Humic acid aqueous dispersions were prepared by dispersing HA sheets in deionized water by mild sonication. Any acidic or ionic impurities in the dispersions were removed by dialysis, which is a crucial step for liquid-crystal formation.

A low-concentration dispersion (typically 0.05-0.6 wt. %) immobilized for a sufficiently long time (usually more than 2 weeks) macroscopically phase-separated into two phases. While the low-density top phase was optically isotropic, the high-density bottom phase demonstrated prominent optical birefringence between two crossed polarizers. A typical nematic schlieren texture consisting of dark and bright brushes was observed in the bottom phase. This is biphasic behavior, where an isotropic phase and nematic phase coexist. The compositional range for the biphase was significantly broad because of the large polydispersity of the HA molecules. It may be noted that ionic strength and pH values significantly influence the stability of HA liquid crystals. The electrostatic repulsion from the dissociated surface functional groups such as carboxylate plays a crucial role in the stability of HA liquid crystals. Thus, reducing repulsive interaction by increasing ionic strength or lowering pH values increased the coagulation of HA sheets.

We observed that substantially all HA sheets form a liquid crystal phase when HA sheets occupy a weight fraction of 1.1%, and the liquid crystals can be preserved by gradually increasing the concentration of HA to the range of from 6% to 16%. The prepared humic acid dispersion exhibited an inhomogeneous, chocolate-milk-like appearance to the naked eye. This milky appearance can be mistaken for aggregation or precipitation of the graphene oxide but, in fact, it is a nematic liquid crystal.

By dispensing and coating the HA suspension on a polyethylene terephthalate (PET) film in a slurry coater and removing the liquid medium from the coated film we obtained a thin film of dried HA. The dried film was peeled off from the PET film to become a free-standing film prior to heat treating. Additionally, HA suspension was also coated on Cu foil or Ti surfaces and then dried. Each film (both the free-standing film peeled off from PET and the Ti- or Cu-supported film) was then subjected to different heat treatments, which typically include a chemical linking and thermal reduction treatment at a first temperature of 80° C. to 300° C. for 1-10 hours, and at a second temperature of 1,500° C.-2,850° C. for 0.5-5 hours. The Cu-supported film and Ti-supported film were heat-treated up to only 1,250° C. and 1,500° C., respectively. With these heat treatments, also under a compressive stress, the HOHA films were transformed into highly conducting graphitic films (HOGF).

The internal structures (crystal structure and orientation) of several dried HA layers (HOHA films), and the HOGF at different stages of heat treatments were investigated. X-ray diffraction curves of a layer of dried HOHA prior to the heat treatment, a HOHA film thermally treated at 150° C. for 5 hours, and the resultant HOGF were obtained. The peak at approximately 2θ=12° of the dried HOHA layer corresponds to an inter-graphene spacing ($d_{002}$) of approximately 0.75 nm. With some heat treatment at 150° C., the dried film exhibits the formation of a hump centered at 22°, indicating that it has begun the process of decreasing the inter-planar spacing, indicating the beginning of chemical linking and ordering processes. With a heat treatment temperature of 2,500° C. for one hour, the $d_{002}$ spacing of the films (not bonded to a metal foil) has decreased to approximately 0.336, close to 0.3354 nm of a graphite single crystal.

With a heat treatment temperature of 2,750° C. for one hour, the $d_{002}$ spacing of the films not bonded to metal surfaces is decreased to approximately 0.3354 nm, identical to that of a graphite single crystal. In addition, a second diffraction peak with a high intensity appears at 2θ=55° corresponding to X-ray diffraction from (004) plane. The (004) peak intensity relative to the (002) intensity on the same diffraction curve, or the I(004)/I(002) ratio, is a good indication of the degree of crystal perfection and preferred orientation of graphene planes. It is well-known in the art that the (004) peak is either non-existing or relatively weak, with the I(004)/I(002) ratio <0.1, for all conventional graphitic materials heat treated at a temperature lower than 2,800° C. The I(004)/I(002) ratio for the graphitic materials heat treated at 3,000-3,250° C. (e.g., highly oriented pyrolytic graphite, HOPG) is in the range from 0.2-0.5. In contrast, a HOGF prepared from the HA liquid crystal-based film with a final HTT of 2,750° C. for one hour exhibits a I(004)/I(002) ratio of 0.77 and a Mosaic spread value of 0.21, indicating a practically perfect graphene single crystal with an exceptionally high degree of preferred orientation.

The "mosaic spread" value is obtained from the full width at half maximum of the (002) reflection in an X-ray diffraction intensity curve. This index for the degree of ordering characterizes the graphite or graphene crystal size (or grain size), amounts of grain boundaries and other defects, and the degree of preferred grain orientation. A nearly perfect single crystal of graphite is characterized by having a mosaic spread value of 0.2-0.4. Most of our HA-derived HOGF have a mosaic spread value in this range of 0.2-0.4 when produced using a final heat treatment temperature no less than 2,500° C.

It may be noted that the I(004)/I(002) ratio for all tens of flexible graphite foil compacts investigated are all <<0.05, practically non-existing in most cases. The I(004)/I(002) ratio for all graphene paper/membrane samples prepared with a vacuum-assisted filtration method is <0.1 even after a heat treatment at 3,000° C. for 2 hours. These observations have further confirmed the notion that the presently invented HOHA film is a new and distinct class of material that is fundamentally different from any pyrolytic graphite (PG), flexible graphite (FG), and paper/film/membrane of conventional graphene/GO/RGO sheets/platelets (NGPs).

Figure 5A:
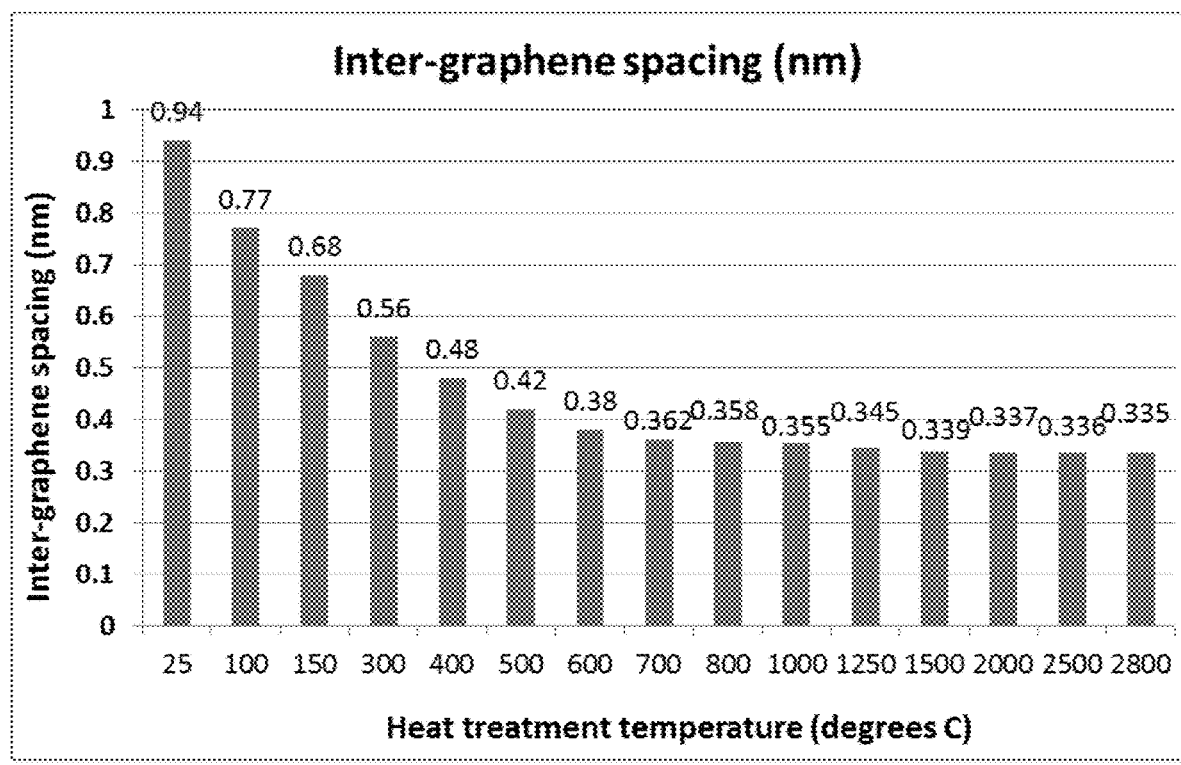
FIG. 5(A) Inter-graphene plane spacing in HA-derived HOGF measured by X-ray diffraction.
Figure 5B:
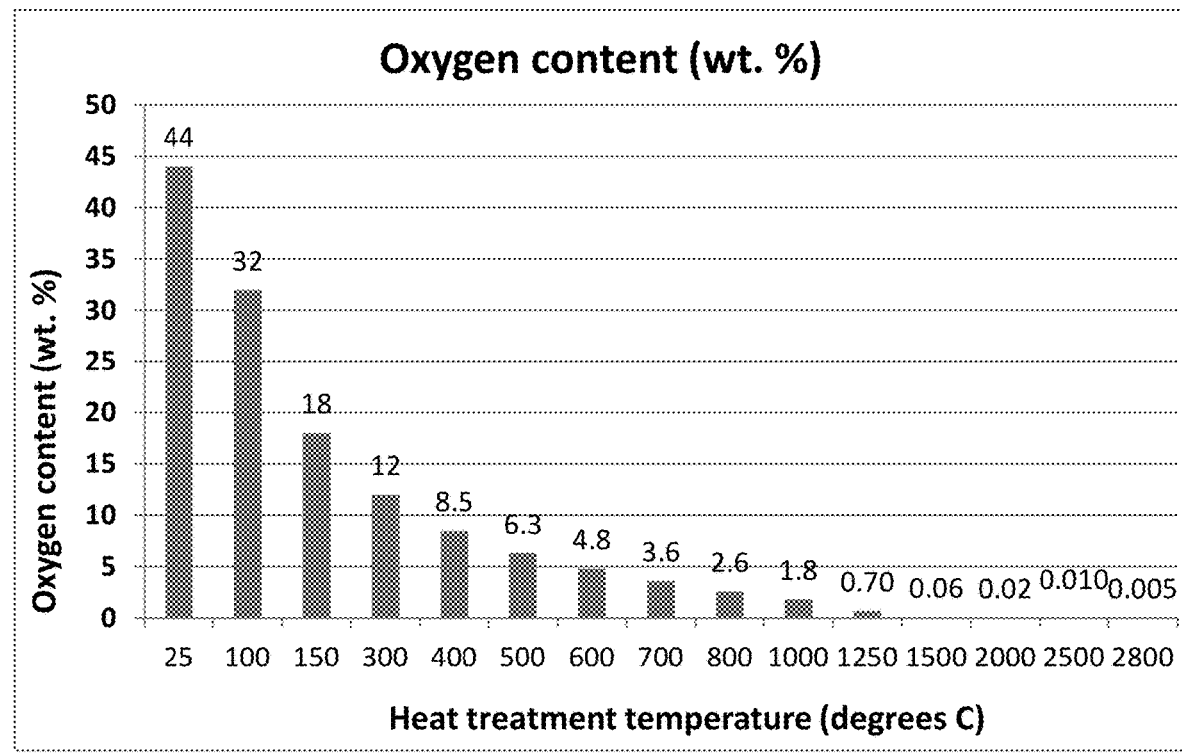
FIG. 5(B) The oxygen content in the HA-derived HOGF.
Figure 5C:
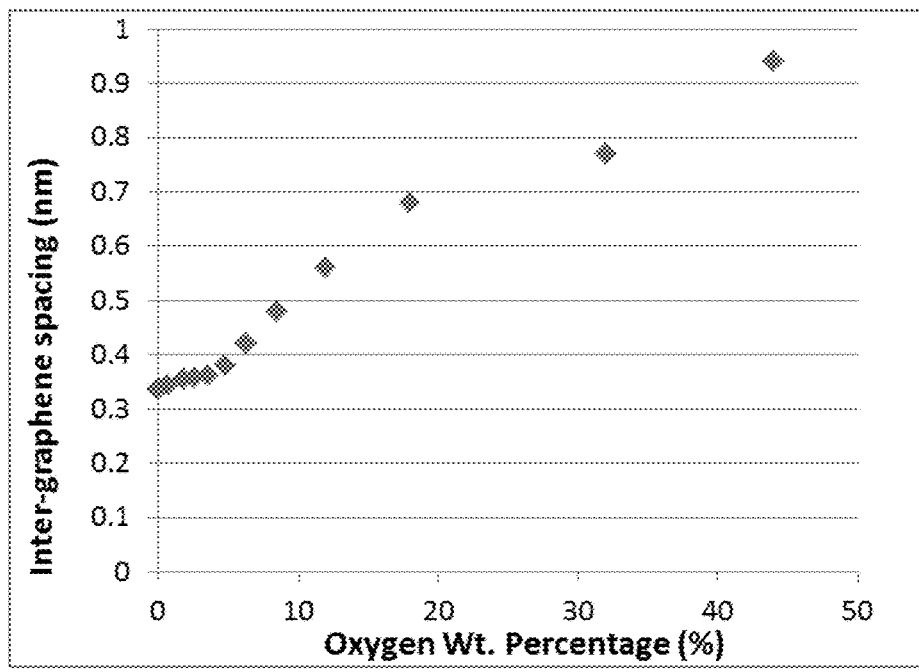
FIG. 5(C) The correlation between inter-graphene spacing and the oxygen content.
Figure 5D:
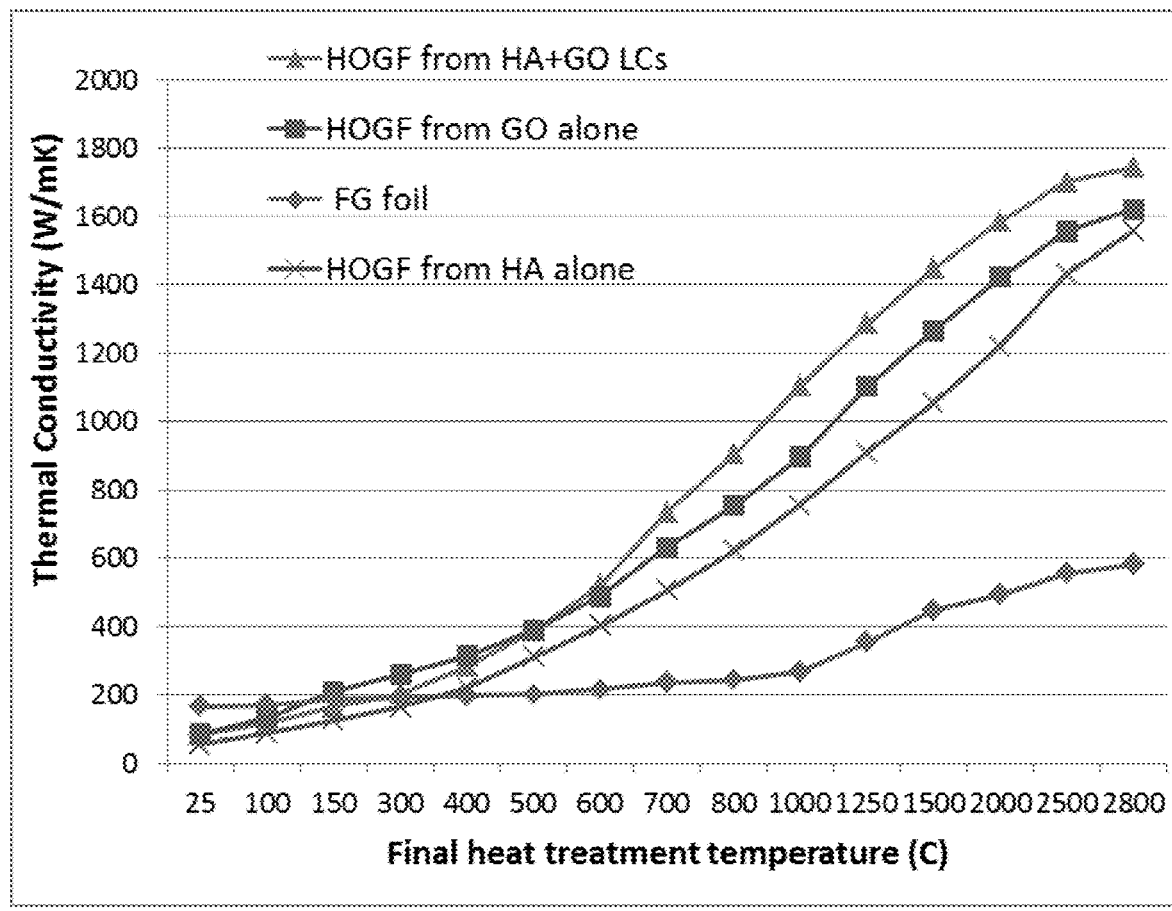
FIG. 5(D) Thermal conductivity values of the HA/GO-derived HOGF, GO-derived HOGF, HA-derived HOGF, and FG foil plotted as a function of the final heat treatment temperature.

The inter-graphene spacing values of both the HA liquid crystal suspension-derived HOGF samples obtained by heat treating at various temperatures over a wide temperature range are summarized in FIG. 5(A). Corresponding oxygen content values are shown in FIG. 5(B). In order to show the correlation between the inter-graphene spacing and the oxygen content, the data in FIG. 5(A) and FIG. 5(B) are re-plotted in FIG. 5(C). A close scrutiny of FIG. 5(A), FIG. 5(B) and FIG. 5(C) indicate that there are four HTT ranges (100-300° C.; 300-1,500° C.; 1,500-2,000° C., and >2,000° C.) that lead to four respective oxygen content ranges and inter-graphene spacing ranges. The thermal conductivity of the HA liquid crystal-derived HOGF specimens and the corresponding sample of flexible graphite (FG) foil sheets, also plotted as a function of the same final heat treatment temperature range, is summarized in FIG. 5(D). All these samples have comparable thickness values.

It is of significance to point out that a heat treatment temperature as low as 500° C. is sufficient to bring the average inter-planar spacing to below 0.4 nm, getting closer and closer to that of natural graphite or that of a graphite single crystal. The beauty of this approach is the notion that this HA liquid crystal suspension strategy has enabled us to re-organize, re-orient, and chemically merge the planar HA sheets into a unified structure with all the graphene-like planes now being larger in lateral dimensions (significantly larger than the length and width of the hexagonal carbon planes in the original HA molecules) and essentially parallel to one another. This has given rise to a thermal conductivity already 300-400 W/mK (with a HTT of 500° C.) and >623 W/mk (from HA only) or >900 W/mk (from mixture of HA+GO) with a HTT of 700° C., which is more than 3- to 4-fold greater than the value (200 W/mK) of the corresponding flexible graphite foil. Furthermore, the tensile strength of the HOGF samples can reach 90-125 MPa (FIG. 7(A)).

Figure 4A:
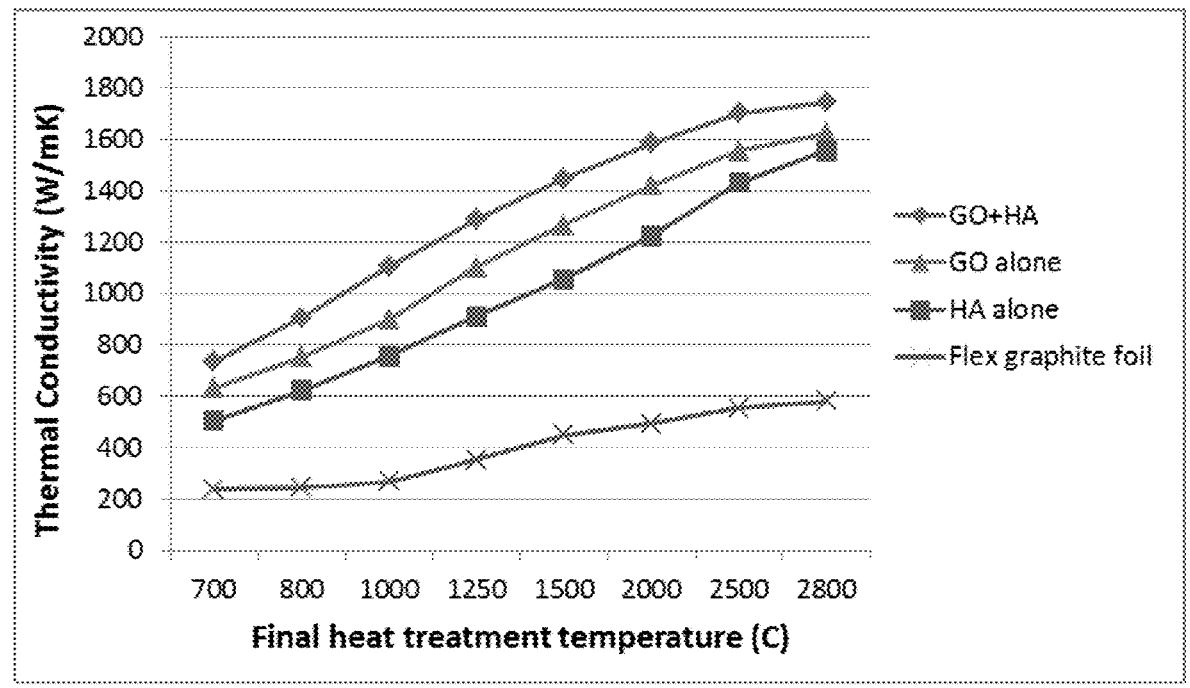
FIG. 4(A) Thermal conductivity values of the HA/GO-derived HOGF, GO-derived HOGF, HA-derived HOGF, and FG foil plotted as a function of the final heat treatment temperature.

With a HTT as low as 1,000° C., the resulting highly oriented HA film exhibits a thermal conductivity of 756 W/mK (from HA alone) and 1,105 W/mK (from a HA-GO mixture), respectively. This is in stark contrast to the observed 268 W/mK of the flexible graphite foil with an identical heat treatment temperature. As a matter of fact, no matter how high the HTT is (e.g. even as high as 2,800° C.), the flexible graphite foil only shows a thermal conductivity lower than 600 W/mK. At a HTT of 2,800° C., the presently invented HOGF layer delivers a thermal conductivity of 1,745 W/mK for a layer derived from a mixture of HA and GO (FIG. 4(A) and FIG. 5(D)). It may be further noted that, as indicated in FIG. 4(A), the thermal conductivity values of HA/GO mixture-derived graphitic films are consistently higher than those of corresponding graphitic films derived from graphene oxide. This surprising effect is further discussed in Example 8.

Scanning electron microscopy (SEM), transmission electron microscopy (TEM) pictures of lattice imaging of the graphene layer, as well as selected-area electron diffraction (SAD), bright field (BF), and dark-field (DF) images were also conducted to characterize the structure of unitary graphene materials. For measurement of cross-sectional views of the film, the sample was buried in a polymer matrix, sliced using an ultra-microtome, and etched with Ar plasma.

Figure 2:
FIG. 2 An SEM image of a cross-section of a flexible graphite foil, showing many graphite flakes with orientations not parallel to the flexible graphite foil surface plane and also showing many defects, kinked or folded flakes.
Figure 3A:
FIG. 3(A) A SEM image of a HA liquid crystal-derived HOGF, wherein multiple hexagonal carbon planes are seamlessly merged into continuous-length graphene-like sheets or layers that can run for tens of centimeters wide or long (only a 50 μm width of a 10-cm wide HOGF being shown in this SEM image)
Figure 3A:
Figure 3B:
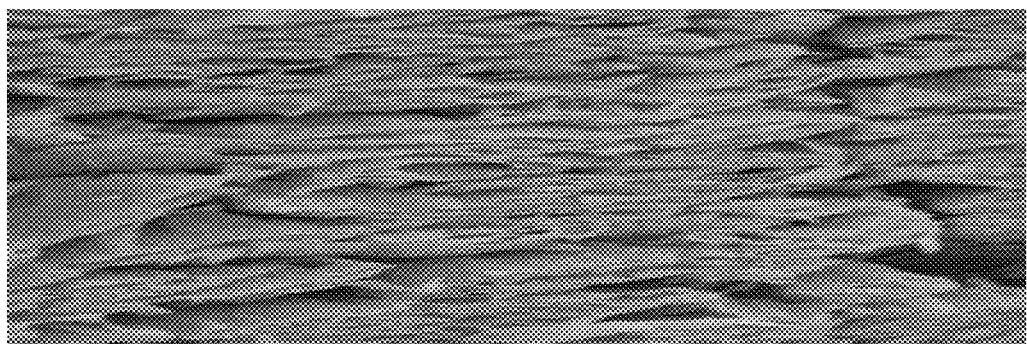
FIG. 3(B) A SEM image of a cross-section of a conventional graphene paper prepared from discrete reduced graphene oxide sheets/platelets using a paper-making process (e.g. vacuum-assisted filtration). The image shows many discrete graphene sheets being folded or interrupted (not integrated), with orientations not parallel to the film/paper surface and having many defects or imperfections.
Figure 3B:
Figure 3C:
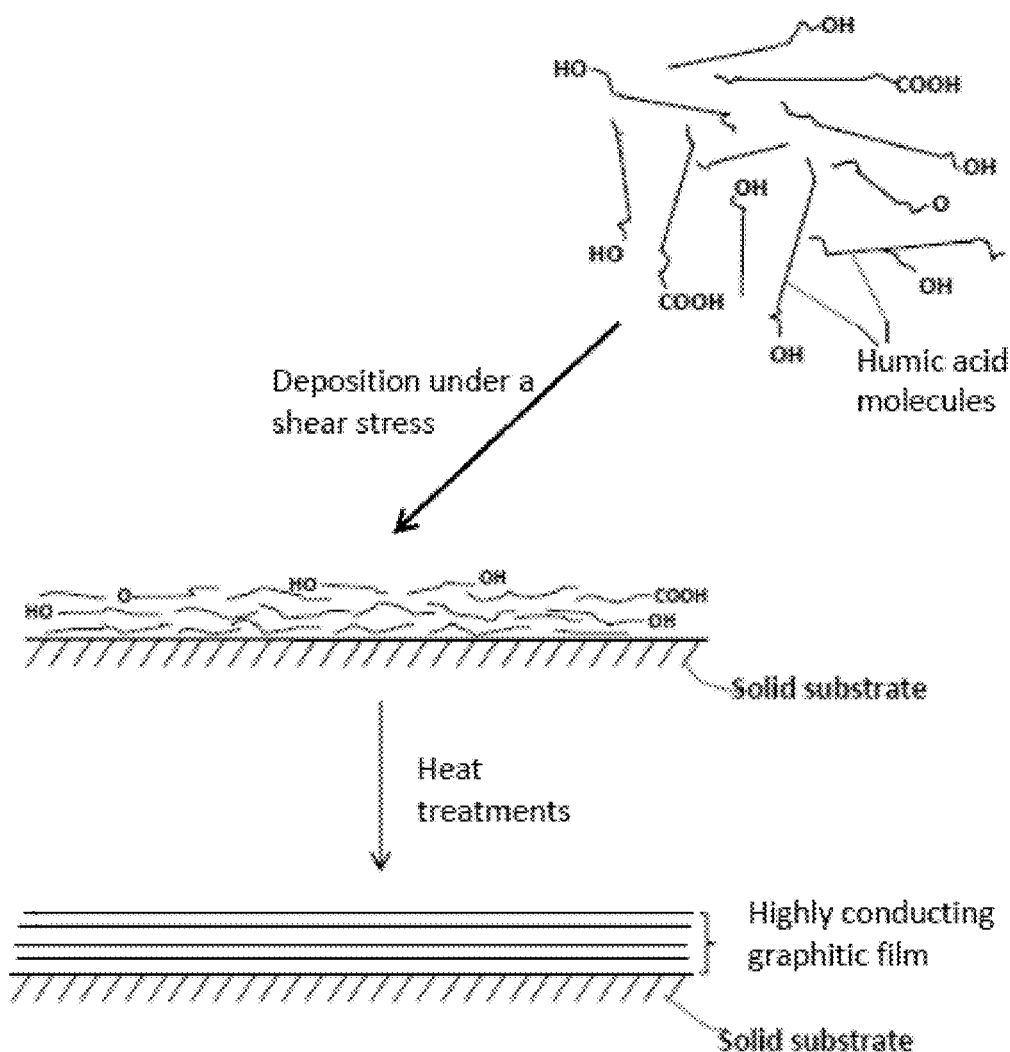
FIG. 3(C) Schematic of a film of highly oriented humic acid molecules being chemically merged together to form a highly ordered and conducting graphitic film.

A close scrutiny and comparison of FIG. 2, FIG. 3(A), and FIG. 3(B) indicates that the graphene-like layers in a HOGF are substantially oriented parallel to one another; but this is not the case for flexible graphite foil and graphene oxide paper. The inclination angles between two identifiable layers in the highly conducting graphitic film are generally less than 10 degrees and mostly less than 5 degrees. In contrast, there are so many folded graphite flakes, kinks, and mis-orientations in flexible graphite that many of the angles between two graphite flakes are greater than 10 degrees, some as high as 45 degrees (FIG. 2). Although not nearly as bad, the mis-orientations between graphene platelets in NGP paper (FIG. 3(B)) are also high and there are many gaps between platelets. The HOGF entity is essentially gap-free.

FIG. 4 (A) shows the thermal conductivity values of the HA/GO-derived film, GO-derived film, HA suspension-derived HOGF, and flexible graphite (FG) foil, respectively, all plotted as a function of the final HTT. These data have clearly demonstrated the superiority of the presently invented HA/GO-derived HOGF structures in terms of the achievable thermal conductivity at a given heat treatment temperature.

1) The HA/GO liquid crystal suspension-derived HOGF appears to be superior to the GO gel-derived HOGF in thermal conductivity at comparable final heat treatment temperatures. The heavy oxidation of graphene sheets in GO gel might have resulted in high defect populations on graphene surfaces even after thermal reduction and re-graphitization. However, the presence of HA molecules seem to be capable of helping to heal the defects or bridging the gaps between GO sheets.
2) Although the highly oriented films derived from HA alone exhibit thermal conductivity values slightly lower than those derived from GO alone, the HA, as a material, is naturally abundant and it does not require the use of undesirable chemicals to produce HA. HA is one order of magnitude less expensive than natural graphite (a raw material for GO) and 2-4 orders of magnitude less expensive than GO.
3) For comparison, we have also obtained conventional highly oriented pyrolytic graphite (HOPG) samples from the polyimide (PI) carbonization route. The polyimide films were carbonized at 500° C. for 1 hour, at 1,000° C. for 3 hours, and at 1,500° C. for 12 hours in an inert atmosphere. The carbonized PI films were then graphitized at a temperature in the range from 2,500-3,000° C., under a compressive force, for 1 to 5 hours to form a conventional HOPG structure.

Figure 4B:
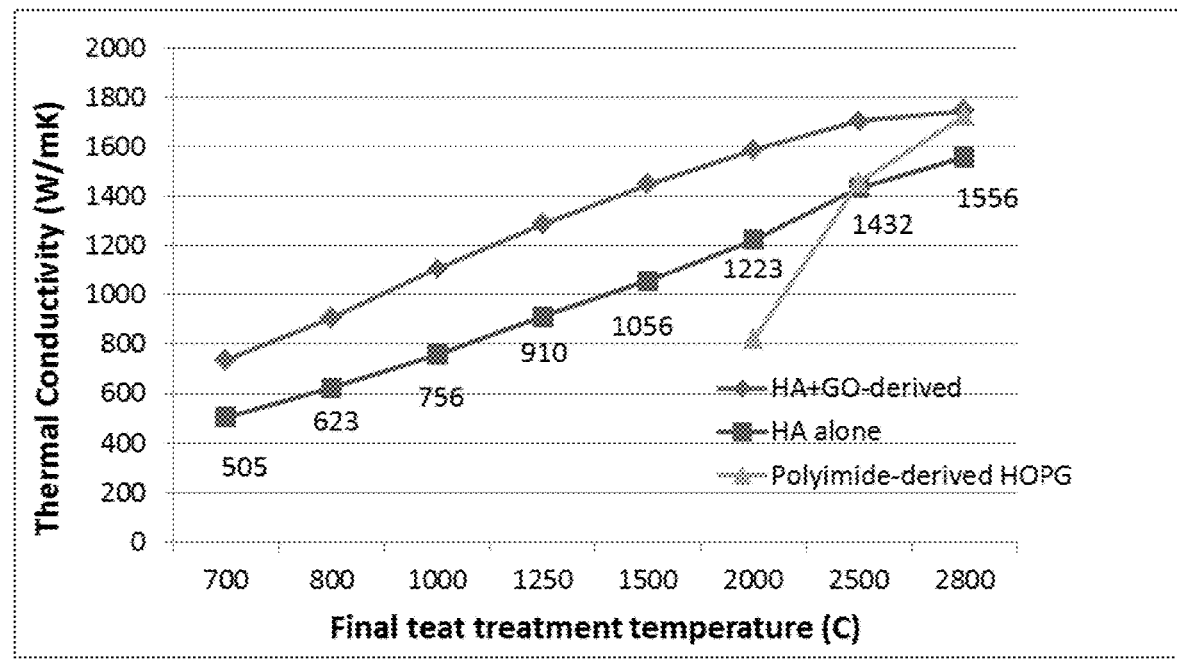
FIG. 4(B) Thermal conductivity values of the HA/GO-derived HOGF, HA-derived HOGF, and polyimide-derived HOPG, all plotted as a function of the final HTT.
Figure 4C:
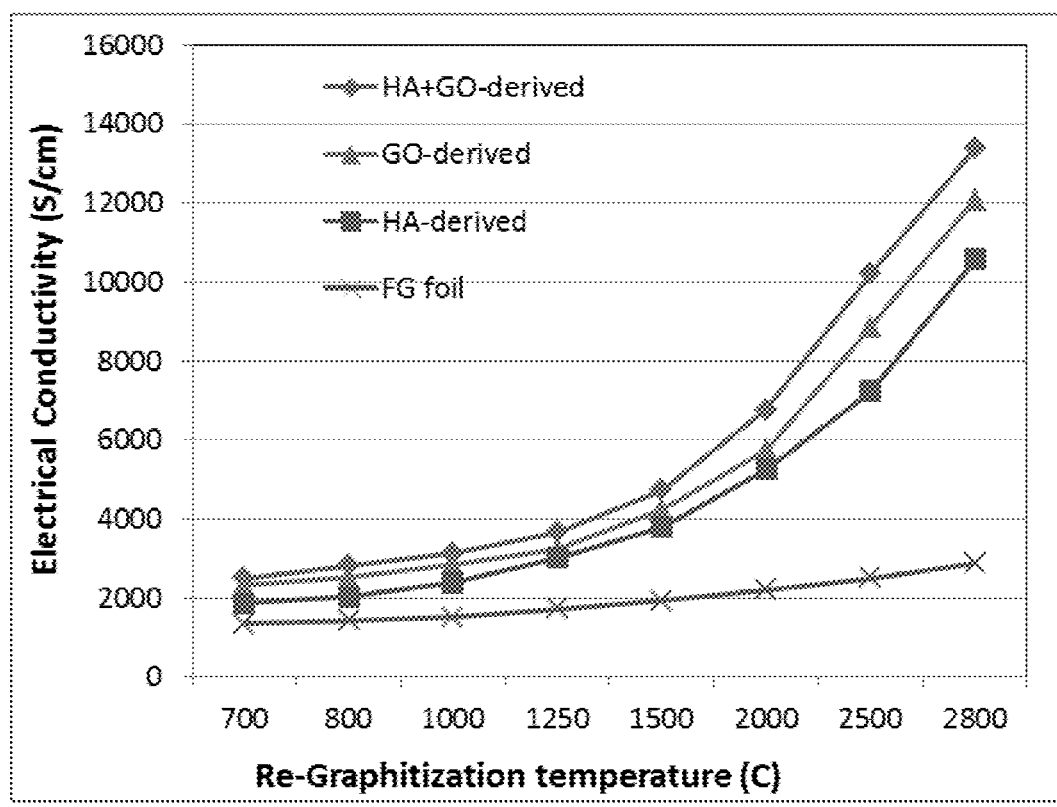
FIG. 4(C) Electric conductivity values of the HA/GO-derived HOGF, GO-derived HOGF, HA-derived HOGF, and FG foil plotted as a function of the final heat treatment temperature.

FIG. 4(B) shows the thermal conductivity values of the HA/GO suspension-derived HOGF, the HA suspension-derived HOGF, and the polyimide-derived HOPG, all plotted as a function of the final heat treatment temperature. These data show that the conventional HOPG, produced by using the carbonized polyimide (PI) route, exhibits a consistently lower thermal conductivity as compared to the HA/GO-derived HOGF, given the same HTT for the same length of heat treatment time. For instance, the HOPG from PI exhibits a thermal conductivity of 820 W/mK after a graphitization treatment at 2,000° C. for 1 hour. At the same final graphitization temperature, the HA/GO-derived HOGF exhibits a thermal conductivity value of 1,586 W/mK. It may be noted that PI is also orders of magnitude more expensive than HA and the production of PI involves the use of several environmentally undesirable organic solvents.
4) These observations have demonstrated a clear and significant advantage of using the HA/GO or HA suspension approach to producing HOGF versus the conventional PG approach to producing oriented graphite crystals. As a matter of fact, no matter how long the graphitization time is for the HOPG, the thermal conductivity is always lower than that of a HA/GO liquid crystal-derived HOGF. It is also surprising to discover that humic acid molecules are capable of chemically linking with one another to form strong and highly conducting graphitic films. It is clear that, the highly oriented HA film (including highly oriented HA/GO film), and the subsequently heat-treated versions are fundamentally different and patently distinct from the flexible graphite (FG) foil, graphene/GO/RGO paper/membrane, and pyrolytic graphite (PG) in terms of chemical composition, crystal and defect structure, crystal orientation, morphology, process of production, and properties.
5) The above conclusion is further supported by the data in FIG. 4(C) showing the electric conductivity values of the HA/GO suspension-derived and HA suspension-derived HOGF HOGF are far superior to those of the FG foil sheets over the entire range of final HTTs investigated.

Figure 6:
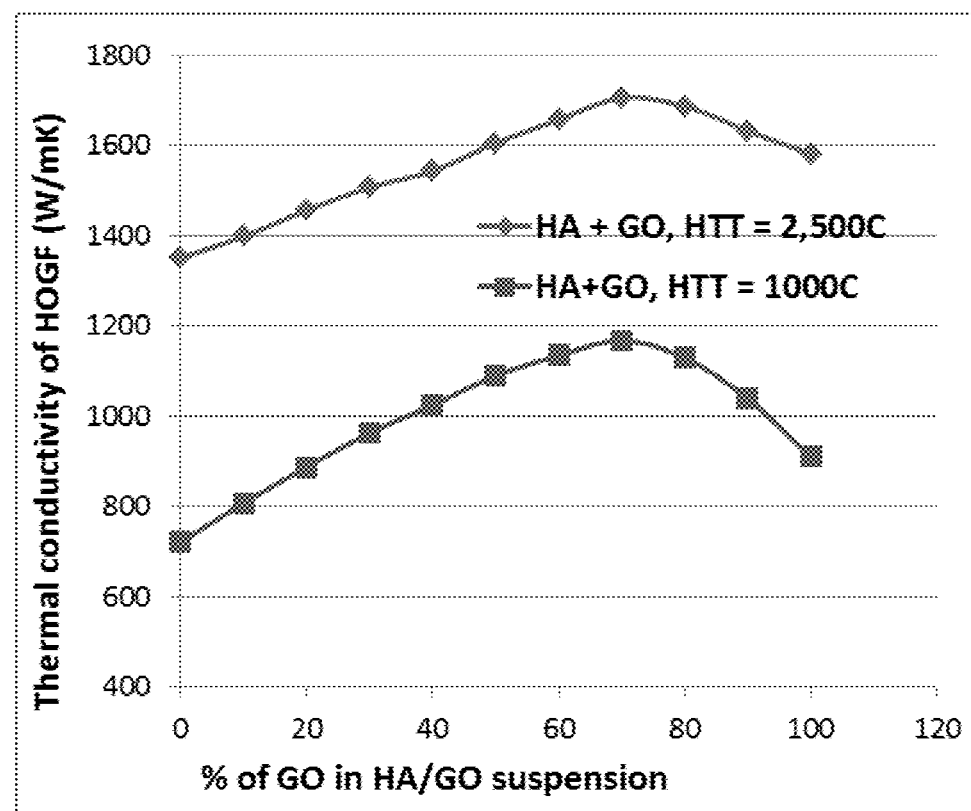
FIG. 6 Thermal conductivity of HOGF samples plotted as a function of the proportion of GO sheets in a HA/GO suspension.

Example 8: The Effect of Graphene Addition on the Properties of HA-Based Highly Oriented Graphitic Films and Graphitic Films Derived Therefrom Various amounts of graphene oxide (GO) sheets were added to HA suspensions to obtain mixture suspensions wherein HA and GO sheets are dispersed in a liquid medium. The same procedure as described above was then followed to produce HOGF samples of various GO proportions. The thermal conductivity data of these samples are summarized in FIG. 6, which indicate that the thermal conductivity values of the HOGF produced from the HA-GO mixtures are higher than those of the HOGF films produced from single-component alone.

Further surprisingly, there are synergistic effects that can be observed when both the HA sheets and GO sheets co-exist in proper proportions. It seems that HA can help GO sheets (known to be highly defected) heal from their otherwise defected structure. It is also possible that HA molecules, being significantly smaller in size than GO sheets/molecules, can fill in the gaps between GO molecules and react therewith to bridge the gaps. These two factors likely lead to the significantly improved conductivity.

Examples 9: Tensile Strength of Various Graphene Oxide-Derived HOHA Films

Figure 7A:
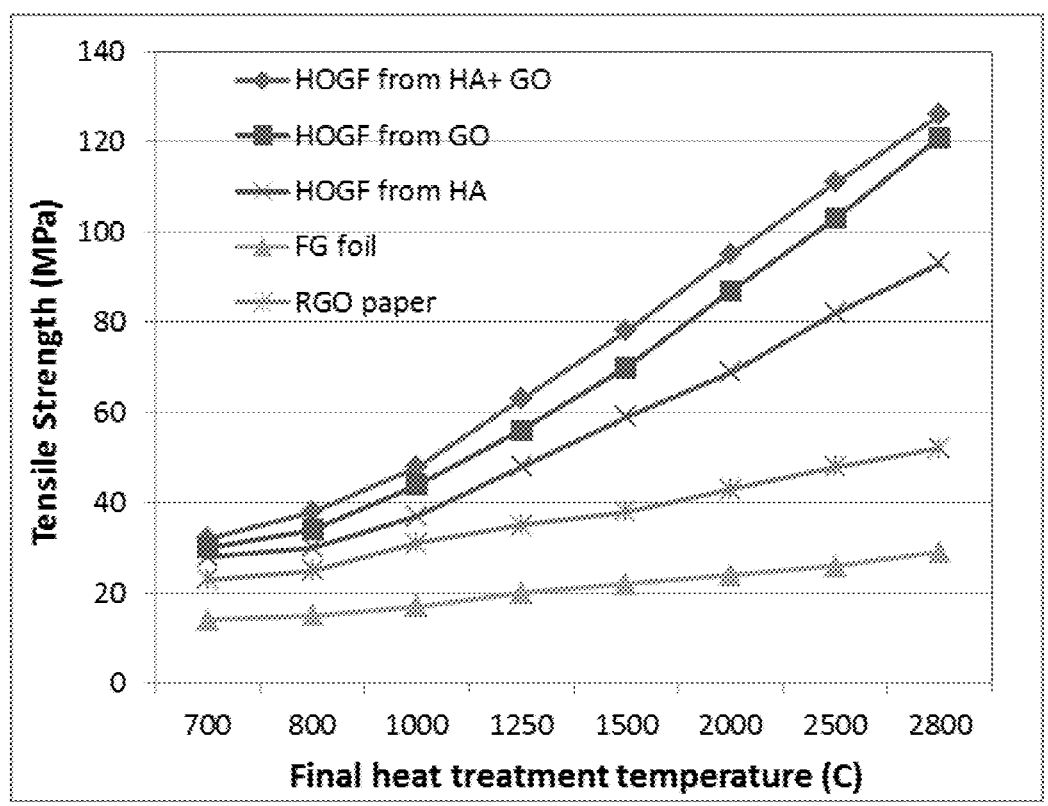
FIG. 7(A) Tensile strength values of HA/GO-derived HOGF, GO-derived HOGF, HA-derived HOGF, flexible graphite foil, and reduced graphene oxide paper, all plotted as a function of the final heat treatment temperature.
Figure 7B:
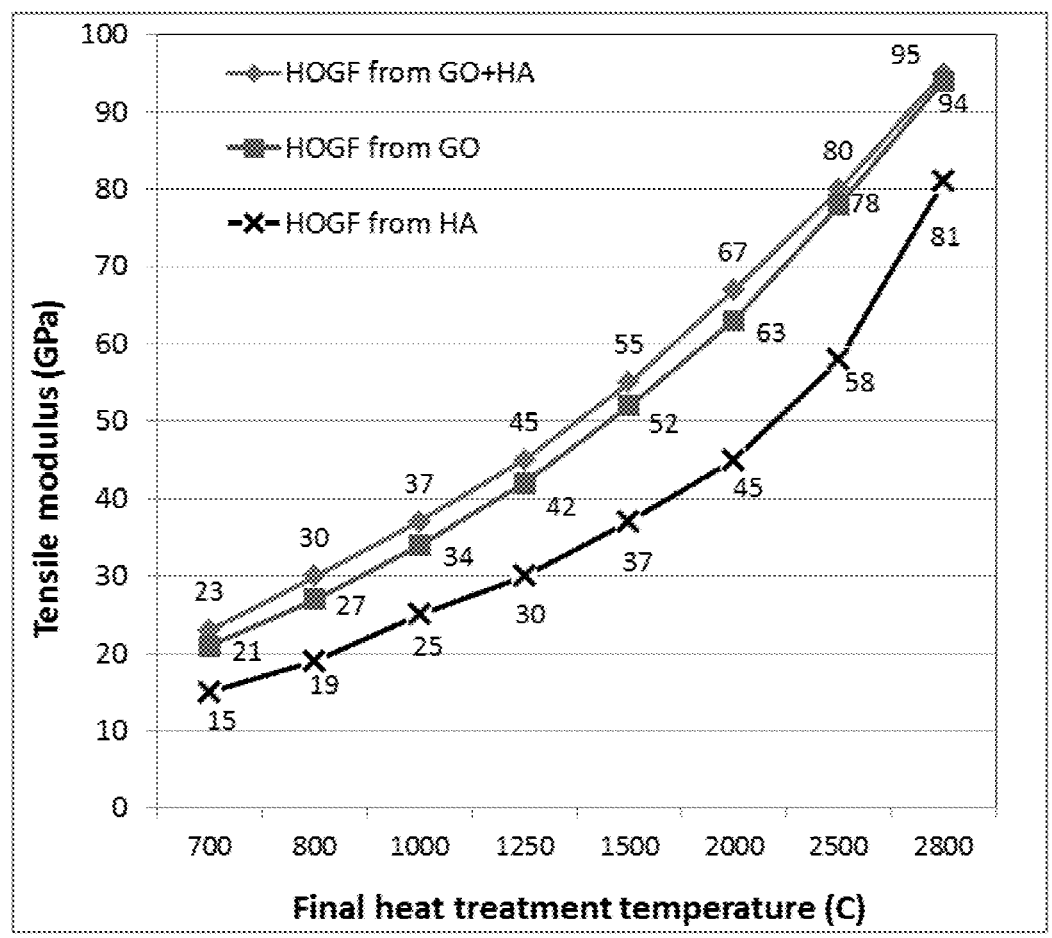
FIG. 7(B) Tensile modulus of the HA/GO-derived HOGF, GO-derived HOGF, and HA-derived HOGF, plotted as a function of the final heat treatment temperature.

A series of HA/GO dispersion-derived HOGF, GO dispersion-derived HOGF, and HA-derived HOGF films were prepared by using a comparable final heat treatment temperature for all materials. A universal testing machine was used to determine the tensile properties of these materials. The tensile strength and modulus of these various samples prepared over a range of heat treatment temperatures are shown in FIG. 7(A) and FIG. 7(B), respectively. For comparison, some tensile strength data of RGO paper and flexible graphite foil are also summarized in FIG. 7(A).

These data have demonstrated that the tensile strength of the graphite foil-derived sheets increases slightly with the final heat treatment temperature (from 14 to 29 MPa) and that of the GO paper (compressed/heated sheets of GO paper) increases from 23 to 52 MPa when the final heat treatment temperature increases from 700 to 2,800° C. In contrast, the tensile strength of the HA-derived HOGF increases significantly from 28 to 93 MPa over the same range of heat treatment temperatures. Most dramatically, the tensile strength of the HA/GO suspension-derived HOGF increases significantly from 32 to 126 MPa. This result is quite striking and further reflects the notion that the HA/GO and HA dispersion contains highly oriented/aligned, chemically active HA/GO and HA sheets/molecules that are capable of chemical linking and merging with one another during the heat treatment, while the graphene platelets in the conventional GO paper and the graphite flakes in the FG foil are essentially dead platelets. The HA or HA/GO-based highly oriented films and the subsequently produced graphitic films is a new class of material by itself.

As a point of reference, the film, obtained by simply spraying HA-solvent solution onto a glass surface and drying the solvent, does not have any strength (it is so fragile that you can break the film by simply touch the film with a finger). After heat treating at a temperature >100° C., this film became fragmented (broken into a huge number of pieces). In contrast, the highly oriented HA film (wherein all HA molecules or sheets are highly oriented and packed together), upon heat treatment at 150° C. for one hour, became a film of good structural integrity, having a tensile strength >24 MPa.

Figure 8:
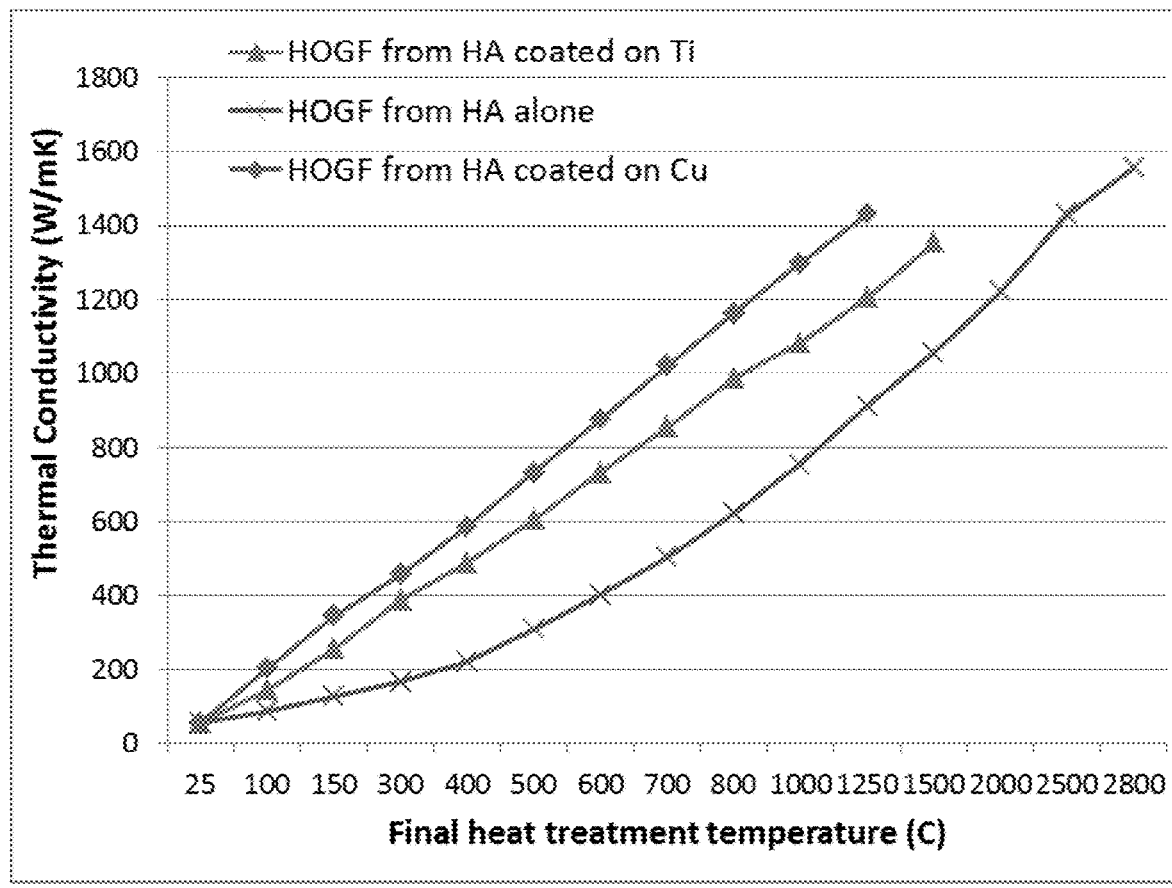
FIG. 8 Thermal conductivity of three HA-derived highly oriented films; one obtained by heat-treating a HA film that was peeled off from a glass surface, one deposited on and bonded to Ti surface while being heat-treated, and one deposited on and bonded to a Cu foil surface while being heat-treated.

Example 10: The Novel Effect of Metal Foil on Heat-Induced Chemical Linking of Humic Acid Molecules Shown in FIG. 8 are the thermal conductivity values of three HA-derived highly oriented films. The first one was obtained by heat-treating a HA film peeled off from a glass surface. The second one was coated on Ti surface and the film was bonded to Ti surface during the heat-treatment. The third one was coated on a Cu foil surface and was bonded to the Cu foil surface during the heat treatment. With the same final heat treatment temperatures, the metal foil-supported HA films exhibit significantly higher thermal conductivity values as compared to those of the films peeled off from PET film surface prior to heat treating. The Cu and Ti foil appear to be capable of providing some kind of catalytic effect on the heat-induced chemical linking or merging between humic acid molecules in intimate contact with Cu or Ti. This is truly unexpected. Even more surprising is the discovery that the differences in conductivity are very large. Furthermore, when supported on Cu foil, a HA film after a heat treatment at 1,250° C. exhibits a thermal conductivity of 1,432 W/mK. The same value was achieved with the HA-derived film after a heat treatment at 2,500° C. for the same length of time without the benefit of being catalyzed by Cu or Ti.

Example 11: Li—S Cell Containing a Humic Acid-Bonded Metal Foil Current Collector at the Anode and at the Cathode Three (3) Li—S cells were prepared and tested, each one having a lithium foil as the anode active material, a sulfur/expanded graphite composite (75/25 wt. ratio) as the cathode active material, 1M of $LiN(CF_3SO_2)_2$ in DOL as the electrolyte, and a Celgard 2400 as the separator. The first cell (a baseline cell for comparison) contains a 10-μm thick Cu foil as the anode current collector and a 20-μm thick Al foil as the cathode current collector. The second cell (another baseline cell for comparison) has a 10-μm thick GO-resin layer as the anode current collector and a sheet of 14-μm RGO-coated Al foil as the cathode current collector. The third cell has a HA-bonded Cu foil (totally 12-μm thick) of the present disclosure as the anode current collector and a sheet of a 20-μm thick HA-coated Al foil as the cathode current collector.

Charge storage capacities were measured periodically and recorded as a function of the number of cycles. The specific discharge capacity herein referred to is the total charge inserted into the cathode during the discharge, per unit mass of the composite cathode (counting the weights of cathode active material, conductive additive or support, and the binder, but excluding the current collectors). The specific energy and specific power values presented in this section are based on the total cell weight (including anode and cathode, separator and electrolyte, current collectors, and packaging materials). The morphological or micro-structural changes of selected samples after a desired number of repeated charging and recharging cycles were observed using both transmission electron microscopy (TEM) and scanning electron microscopy (SEM).

Figure 9A:
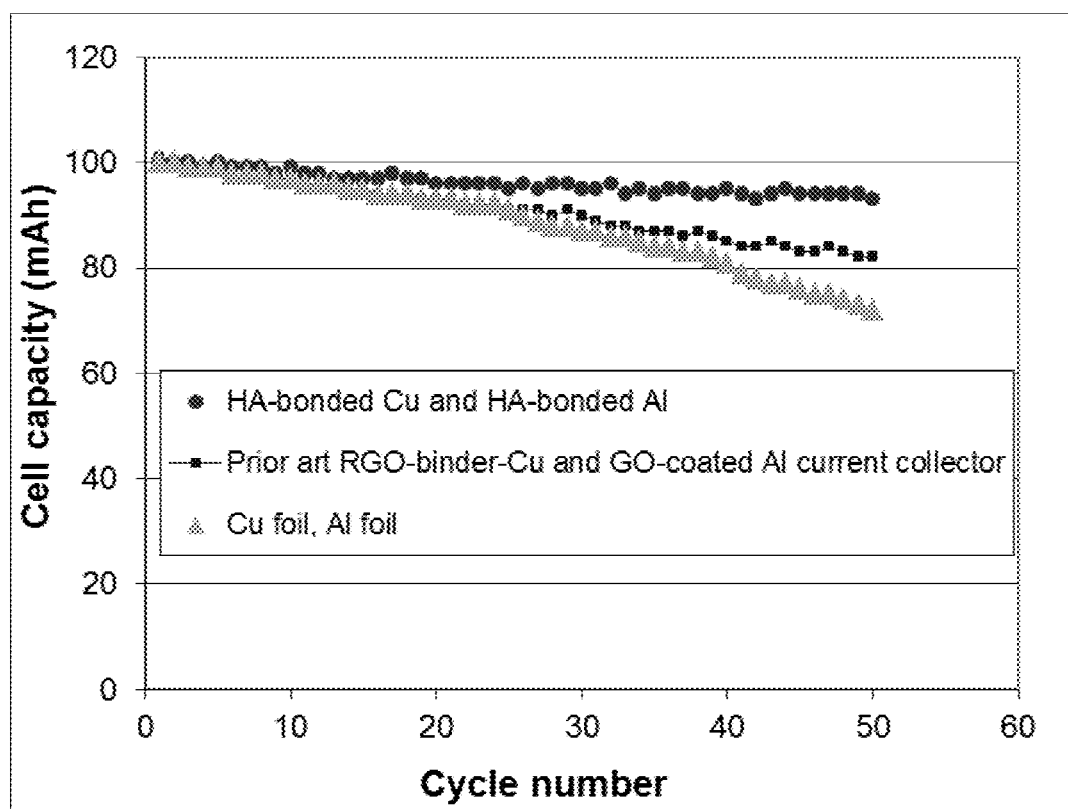
FIG. 9(A) The discharge capacity values of three Li—S cells each as a function of the charge/discharge cycle number; first cell having HA-bonded Cu foil and HA-bonded Al foil as the anode and cathode current collectors, respectively; second cell having GO/resin-coated Cu foil and GO-coated Al foil (no pre-etching) as the anode and cathode current collector, respectively (a prior art cell); third cell having a Cu foil anode current collector and Al foil cathode current collector (a prior art cell).

FIG. 9(A) shows the discharge capacity values of the three cells each as a function of the charge/discharge cycle number. Each cell was designed to have an initial cell capacity of 100 mAh to facilitate comparison. It is clear that the Li—S cell featuring the presently invented HA-bonded current collector at both the anode and the cathode exhibits the most stable cycling behavior, experiencing a capacity loss of 6% after 50 cycles. The cell containing GO/resin-coated Cu and GO-coated Al current collector suffers from a 23% capacity decay after 50 cycles. The cell containing a Cu foil anode current collector and an Al foil cathode current collector suffers from a 26% capacity decay after 50 cycles. Post-cycling inspection of the cells indicate that the Al foil in all prior art electrodes suffered a severe corrosion problem. In contrast, the presently invented humic acid oxide-bonded Al current collectors remain intact.

Figure 9B:
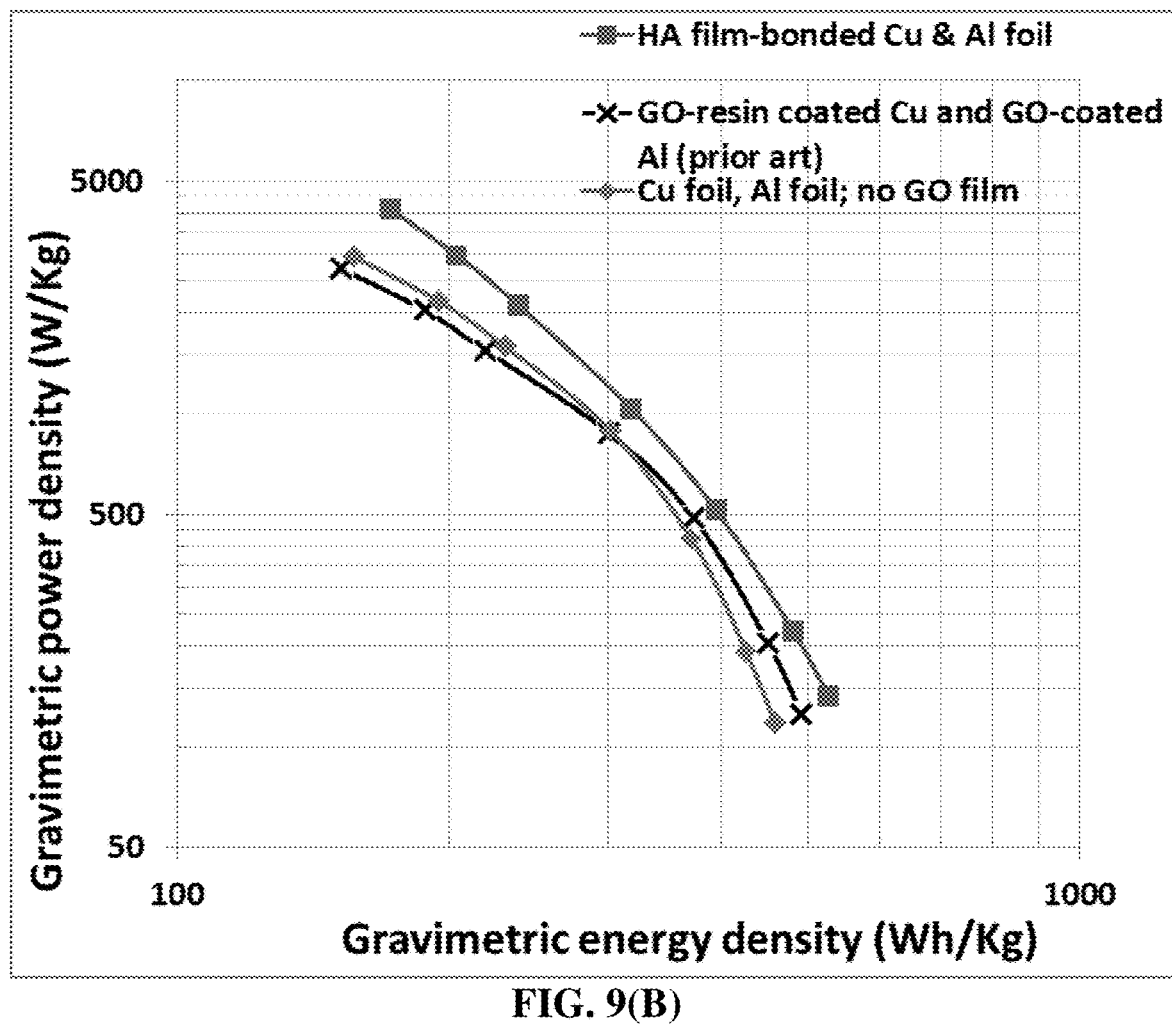
FIG. 9(B) Ragone plots of the three cells: first cell having HA-bonded Cu foil and HA-bonded Al foil as the anode and cathode current collectors, respectively; second cell having GO/resin-coated Cu foil and GO-coated Al foil (no pre-etching) as the anode and cathode current collector, respectively (a prior art cell); third cell having a Cu foil anode current collector and Al foil cathode current collector (a prior art cell).

FIG. 9(B) shows the Ragone plots (gravimetric power density vs. gravimetric energy density) of the three cells. It is of interest to note that our HA-bonded metal foil current collectors surprisingly impart both higher energy density and higher power power density to the Li—S cell compared to prior art graphene/resin-coated current collector at the anode (with GO-coated Al foil at the cathode), and Cu/Al current collectors. This is quite unexpected considering that Cu foil has an electrical conductivity that is more than one order of magnitude higher than that of the graphene film and HA film.

Example 12: Magnesium-Ion Cell Containing a HA-Enabled Current Collector at the Anode and at the Cathode For the preparation of a cathode active material (Magnesium Manganese Silicate, $Mg_{1.03}Mn_{0.97}SiO_4$), reagent-grade KCl (melting point=780° C.) was used as flux after drying for 3 h at 150° C. under vacuum. The starting materials were magnesium oxide (MgO), manganese (II) carbonate ($MnCO_3$) and silicon dioxide ($SiO_2$, 15-20 nm) powder. The stoichiometric amounts for the precursor compounds were controlled with the molar ratio of 1.03:0.97:1 for Mg:Mn:Si. The mixture (flux/reactants molar ratio=4) was hand-ground in a mortar by pestle for a 10 minutes, and then poured into a corundum crucible. Then, the powder mixture was dried at 120° C. for 5 h in a vacuum to minimize the water content in the mixture. Subsequently, the mixture was immediately transferred to a tube furnace and heated in a reductive atmosphere (Ar+5 wt % H2) at 350° C. for 2 h to remove carbonate groups. This was followed by final firing at various temperatures at a rate of 2° C./min for 6 h, then cooling to room temperature naturally. Finally, the product (Magnesium Manganese Silicate, $Mg_{1.03}Mn_{0.97}SiO_4$) was washed three times with deionized water to dissolve any remaining salt, separated by centrifugation, and dried under vacuum at 100° C. for 2 h.

The electrodes (either the anode or cathode) were typically prepared by mixing 85 wt % of an electrode active material (e.g. $Mg_{1.03}Mn_{0.97}SiO_4$ particles, 7 wt % acetylene black (Super-P), and 8 wt % polyvinylidene fluoride binder (PVDF, 5 wt % solid content dissolved in N-methyl-2-pyrrolidinoe (NMP)) to form a slurry-like mixture. After coating the slurry on an intended current collector, the resulting electrode was dried at 120° C. in vacuum for 2 h to remove the solvent before pressing. Three cells having different current collectors were investigated: first cell having HA-bonded Cu foil and HA-bonded Al foil as the anode and cathode current collectors, respectively; second cell having GO/resin-coated Cu foil and GO-coated Al foil (no pre-etching) as the anode and cathode current collector, respectively (a prior art cell); third cell having a Cu foil anode current collector and Al foil cathode current collector (a prior art cell).

Subsequently, the electrodes were cut into disks (diameter=12 mm) for use as a cathode. A thin sheet of magnesium foil was attached to the anode current collector surface, and a piece of porous separator (e.g., Celgard 2400 membrane) was, in turn, stacked on top of the magnesium foil. A piece of cathode disc coated on a cathode current collector was used as a cathode and stacked over the separator layer to form a CR2032 coin-type cell. The electrolyte used was 1 M of $Mg(AlCl_2EtBu)_2$ in THF. The cell assembly was performed in an argon-filled glove-box. The CV measurements were carried out using a CHI-6 electrochemical workstation at a scanning rate of 1 mV/s. The electrochemical performance of the cells was also evaluated by galvanostatic charge/discharge cycling at a current density of from 50 mA/g to 10 A/g (up to 100 A/g for some cells), using an Arbin and/or a LAND electrochemical workstation.

Figure 10:
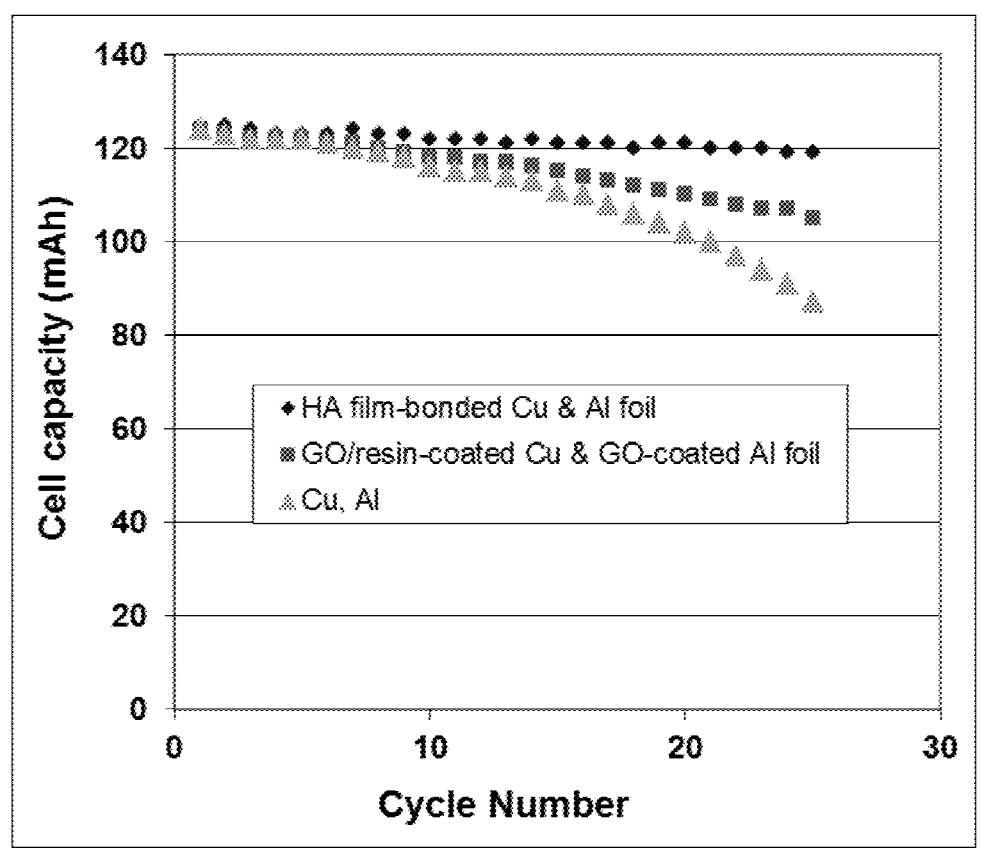
FIG. 10 The cell capacity values of three magnesium metal cells; first cell having HA-bonded Cu foil and HA-bonded Al foil as the anode and cathode current collectors, respectively; second cell having GO/resin-coated Cu foil and GO-coated Al foil (no pre-etching) as the anode and cathode current collector, respectively (a prior art cell); third cell having a Cu foil anode current collector and Al foil cathode current collector (a prior art cell).

FIG. 10 shows the cell discharge specific capacity values of the three cells each as a function of the charge/discharge cycle number. It is clear that the Mg-ion cell featuring the presently invented current collectors at both the anode and the cathode exhibits the most stable cycling behavior, experiencing a capacity loss of 2.5% after 25 cycles. The cell containing GO/resin-coated Cu foil and GO-coated Al foil current collectors suffers from a 17% capacity decay after 25 cycles. The cell containing a Cu foil anode current collector and an Al foil cathode current collector suffers from a 30% capacity decay after 25 cycles. Post-cycling inspection of the cells indicate that GO/resin-coated Cu foil and GO-coated Al foil current collectors got swollen and showed some delamination from the cathode layer and that Al foil suffered a severe corrosion problem. In contrast, inventive HA-bonded metal foil current collectors remain intact.

Example 13: Chemical and Mechanical Compatibility Testing of Various Current Collectors for Various Intended Batteries or Supercapacitors As demonstrated in Examples 11 and 12 above, long-term stability of a current collector relative to the electrolyte of a battery or supercapacitor is a major concern. In order to understand the chemical stability of various current collectors, a major task was undertaken to expose current collectors in several representative electrolytes. After an extended period of time (e.g. 30 days), the current collector was removed from the electrolyte solution and observed using optical and scanning electron microscopy (SEM). The results are summarized in Table 3 below, which consistently demonstrate that the inventive HA-bonded metal foil current collectors are highly compatible with all kinds of liquid electrolytes commonly used in batteries and supercapacitors. The inventive materials are resistant to any chemical attack. These HA-protected current collectors are essentially electrochemically inert over a voltage range of 0-5.5 volts Vs. $Li/Li^+$, suitable for use with just about any battery/capacitor electrolyte.

It may be noted that each current collector must be connected to a tab that is, in turn, connected to an external circuit wire. The current collector must be mechanically compatible with the tab, being readily or easily fastened or bonded thereto. We have found that CVD graphene films just cannot be mechanically fastened to the tab without being easily broken or fractured. Even with the assistance of adhesive, the CVD film is easily fractured during the procedures of connecting to a tab or battery cell packaging.

TABLE 3

Results of current collector-electrolyte compatibility testing.

| Sample No. | Intended battery or supercapacitor | Current collector | Electrolyte | Observations |
| --- | --- | --- | --- | --- |
| Li-1A | Li-ion or Li metal | HA film-bonded Cu foil | 1M $LiPF_6$ in PC + DME | Remains intact, no swelling, no micro-cracking; no pits. |
| Li-1B | Li-ion or Li metal | CVD graphene film | 1M $LiPF_6$ in PC + DME | Micro-cracks formed along grain boundaries |
| Li-1C | Li-ion or Li metal | RGO coated on PET film | 1M $LiPF_6$ in PC + DME | RGO layer swollen, delamination from PET film |
| Na-1A | Na-ion or Na metal | HA film-bonded Ti foil | 1M $NaClO_4$ in DOL + DEC | Remains intact, no swelling, no micro-cracking |
| Na-1B | Na-ion or Na metal | CVD graphene film | 1M $NaClO_4$ in DOL + DEC | Micro-cracks formed along grain boundaries |
| Sup-1A | Supercapacitor or hybrid | HA film-bonded Al foil | 1M $H_2SO_4$ in water | Remains intact, no swelling, no micro-cracking |
| Sup-1B | Supercapacitor or hybrid | Flexible graphite foil | 1M $H_2SO_4$ in water | Severely swollen, flaking (graphite flakes coming off) |
| Sup-1C | Supercapacitor or hybrid | HA film-bonded Al foil | Alkylammonium in acetonitrile | Remains intact, no swelling, no micro-cracking, no pitting corrosion |
| Sup-1D | Supercapacitor or hybrid | Carbon-coated Al | Alkylammonium in acetonitrile | Corrosion of Al layer; some carbon flaking |
| Zn-1A | Zinc-air | HA film-bonded Ni foil | KOH in water | Remains intact, no swelling, no micro-cracking |
| Zn-1B | Zinc-air | Flexible graphite foil | KOH in water | Severely swollen, flaking |

In conclusion, we have successfully developed an absolutely new, novel, unexpected, and patently distinct class of highly conducting material: humic acid-derived thin film-bonded on metal foil surface(s). The chemical composition, structure (crystal perfection, grain size, defect population, etc), crystal orientation, morphology, process of production, and properties of this new class of materials are fundamentally different and patently distinct from flexible graphite foil, polymer-derived pyrolytic graphite, CVD-derived PG (including HOPG), and catalytic CVD graphene thin film that are free-standing or coated on a metal foil. The thermal conductivity, electrical conductivity, scratch resistance, surface hardness, and tensile strength exhibited by the presently invented materials are much higher than what prior art flexible graphite sheets, paper of discrete graphene/GO/RGO platelets, or other graphitic films could possibly achieve. These HA-derived thin film structures have the best combination of excellent electrical conductivity, thermal conductivity, mechanical strength, surface scratch resistance, hardness, and no tendency to flake off.

The invention claimed is:

1. A chemically functionalized humic acid-bonded metal foil current collector for use in a battery or supercapacitor, said current collector comprising:
   (a) a thin metal foil having a thickness from 1 μm to 30 μm and two opposed but substantially parallel primary surfaces; and
   (b) at least one thin film comprising chemically functionalized humic acid, wherein said thin film comprising chemically functionalized humic acid is chemically bonded to at least one of said two opposed primary surfaces of said metal foil;
   wherein said thin film comprising chemically functionalized humic acid has a thickness from 5 nm to 10 μm, an oxygen content from 0.01% to 10% by weight, a physical density from 1.3 to 2.2 $g/cm^3$, chemically functionalized humic acid sheets being oriented substantially parallel to each other and parallel to said primary surfaces, an inter-planar spacing of 0.335 to 0.50 nm between hexagonal carbon planes, a thermal conductivity greater than 250 W/mK, and an electrical conductivity greater than 800 S/cm when measured alone without said thin metal foil;
   wherein said humic acid is chemically functionalized with a functional group selected from a polymer, $SO_3H$, COOH, $NH_2$, OH, R'CHOH, CHO, CN, COCl, halide, COSH, SH, COOR', SR', $SiR'_3$, $Si(-OR'-)_yR'_3-y$, $Si(-O-SiR'_2-)OR'$, R", Li, $AlR'_2$, Hg—X, $TlZ_2$ and Mg—X; wherein y is an integer equal to or less than 3, R' is hydrogen, alkyl, aryl, cycloalkyl, or aralkyl, cycloaryl, or poly(alkylether), R" is fluoroalkyl, fluoroaryl, fluorocycloalkyl, fluoroaralkyl or cycloaryl, X is halide, and Z is carboxylate or trifluoroacetate, or a combination thereof.

2. The chemically functionalized humic acid-bonded metal foil current collector of claim 1, wherein said thin film further includes graphene sheets.

3. A chemically functionalized humic acid-bonded metal foil current collector for use in a battery or supercapacitor, said current collector comprising:
   (a) a thin metal foil having a thickness from 1 μm to 30 μm and two opposed but substantially parallel primary surfaces; and
   (b) at least one thin film comprising chemically functionalized humic acid and graphene sheets, wherein said thin film comprising chemically functionalized humic acid is chemically bonded to at least one of said two opposed primary surfaces of said metal foil;
   wherein said thin film comprising chemically functionalized humic acid has a thickness from 5 nm to 10 μm, an oxygen content from 0.01% to 10% by weight, a physical density from 1.3 to 2.2 $g/cm^3$, chemically functionalized humic acid sheets being oriented substantially parallel to each other and parallel to said primary surfaces, an inter-planar spacing of 0.335 to 0.50 nm between hexagonal carbon planes, a thermal conductivity greater than 250 W/mK, and an electrical conductivity greater than 800 S/cm when measured alone without said thin metal foil;
   wherein said graphene sheets are selected from pristine graphene, graphene oxide, reduced graphene oxide, graphene fluoride, graphene bromide, graphene iodide, boron-doped graphene, nitrogen-doped graphene, chemically functionalized graphene, or a combination thereof.

4. The chemically functionalized humic acid-bonded metal foil current collector of claim 3, wherein said thin film further includes a polymer.

* * * * *